(12) United States Patent
McGarry et al.

(10) Patent No.: US 8,460,357 B2
(45) Date of Patent: Jun. 11, 2013

(54) IN SITU STENT FORMATION

(75) Inventors: Michael C. McGarry, Truckee, CA (US); Craig Welk, Tracy, CA (US)

(73) Assignee: J.W. Medical Systems Ltd., Palo Alto, CA (US)

( * ) Notice: Subject to any disclaimer, the term of this patent is extended or adjusted under 35 U.S.C. 154(b) by 0 days.

(21) Appl. No.: 11/142,788

(22) Filed: May 31, 2005

(65) Prior Publication Data

US 2006/0271151 A1    Nov. 30, 2006

(51) Int. Cl.
*A61F 2/06* (2006.01)

(52) U.S. Cl.
USPC ........................................ 623/1.11; 623/1.21

(58) Field of Classification Search
USPC ...... 623/1.11, 1.21, 1.12, 1.15, 1.18; 606/191, 606/192, 194, 1.12; 604/101.05, 509, 103.01, 604/103.02
See application file for complete search history.

(56) References Cited

U.S. PATENT DOCUMENTS

| | | | |
|---|---|---|---|
| 5,059,211 A | 10/1991 | Stack et al. | |
| 5,147,385 A | 9/1992 | Beck et al. | |
| 5,213,580 A | 5/1993 | Slepian et al. | |
| 5,246,421 A | 9/1993 | Saab | |
| 5,549,551 A * | 8/1996 | Peacock et al. | 604/103.05 |
| 5,571,086 A | 11/1996 | Kaplan et al. | |
| 5,628,730 A * | 5/1997 | Shapland et al. | 604/21 |
| 5,670,161 A | 9/1997 | Healy et al. | |
| 5,697,948 A | 12/1997 | Marin et al. | |
| 5,749,922 A | 5/1998 | Slepian et al. | |
| 5,776,141 A | 7/1998 | Klein et al. | |
| 5,792,106 A * | 8/1998 | Mische | 604/103.01 |
| 5,855,563 A | 1/1999 | Kaplan et al. | |
| 5,899,917 A * | 5/1999 | Edwards et al. | 606/195 |
| 5,947,977 A | 9/1999 | Slepian et al. | |
| 6,027,510 A * | 2/2000 | Alt | 606/108 |
| 6,039,757 A * | 3/2000 | Edwards et al. | 623/1.21 |
| 6,143,016 A | 11/2000 | Bleam et al. | |
| 6,258,117 B1 | 7/2001 | Camrud et al. | |
| 6,290,485 B1 * | 9/2001 | Wang | 425/470 |
| 6,299,597 B1 * | 10/2001 | Buscemi et al. | 604/101.03 |
| 6,371,975 B2 | 4/2002 | Cruise et al. | |
| 6,485,500 B1 * | 11/2002 | Kokish et al. | 606/194 |
| 6,607,553 B1 | 8/2003 | Healy et al. | |
| 6,623,519 B2 | 9/2003 | Edwin et al. | |
| 6,706,013 B1 * | 3/2004 | Bhat et al. | 604/96.01 |
| 6,830,756 B2 | 12/2004 | Hnojewyj | |
| 7,077,836 B2 * | 7/2006 | Lary et al. | 604/509 |
| 7,137,993 B2 | 11/2006 | Acosta et al. | |
| 7,147,655 B2 | 12/2006 | Chermoni | |
| 7,147,656 B2 | 12/2006 | Andreas et al. | |
| 7,175,653 B2 | 2/2007 | Gaber | |
| 7,182,779 B2 | 2/2007 | Acosta et al. | |
| 7,192,440 B2 | 3/2007 | Andreas et al. | |
| 2002/0029031 A1 * | 3/2002 | Bagaoisan et al. | 604/509 |
| 2003/0130683 A1 | 7/2003 | Andreas et al. | |
| 2003/0135258 A1 | 7/2003 | Andreas et al. | |
| 2003/0135266 A1 * | 7/2003 | Chew et al. | 623/1.16 |
| 2003/0149468 A1 * | 8/2003 | Wallsten | 623/1.11 |
| 2003/0181856 A1 * | 9/2003 | Goldman | 604/103.01 |
| 2004/0093061 A1 | 5/2004 | Acosta et al. | |

(Continued)

*Primary Examiner* — Thomas McEvoy
(74) *Attorney, Agent, or Firm* — Levine Bagade Han LLP

(57) ABSTRACT

Apparatus and methods for delivering stents and other prostheses to body lumens include a prosthesis forming and deploying mechanism carried at the distal end of a catheter shaft. The mechanism is adapted to form and deploy prostheses of a variable length, and to form and deploy multiple prostheses during a single interventional procedure.

17 Claims, 20 Drawing Sheets

U.S. PATENT DOCUMENTS

| | | |
|---|---|---|
| 2004/0098081 A1 | 5/2004 | Landreville et al. |
| 2004/0186551 A1 | 9/2004 | Kao et al. |
| 2004/0215312 A1 | 10/2004 | Andreas |
| 2004/0215331 A1 | 10/2004 | Chew et al. |
| 2004/0230316 A1* | 11/2004 | Cioanta et al. ............ 623/23.66 |
| 2004/0249434 A1 | 12/2004 | Andreas et al. |
| 2004/0249435 A1 | 12/2004 | Andreas |
| 2005/0010276 A1 | 1/2005 | Acosta et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085888 A1 | 4/2005 | Andreas et al. |
| 2005/0149159 A1 | 7/2005 | Andreas et al. |
| 2005/0222603 A1 | 10/2005 | Andreas et al. |
| 2005/0228477 A1 | 10/2005 | Grainger et al. |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0089701 A1 | 4/2006 | Forsyth et al. |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0271150 A1 | 11/2006 | Andreas et al. |
| 2006/0271151 A1 | 11/2006 | McGarry et al. |
| 2006/0282147 A1 | 12/2006 | Andreas |
| 2006/0282148 A1 | 12/2006 | Hammersmark et al. |
| 2006/0282150 A1 | 12/2006 | Olson et al. |
| 2007/0027521 A1 | 2/2007 | Andreas et al. |
| 2007/0087012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2008/0282149 A1 | 12/2008 | Kao |

* cited by examiner

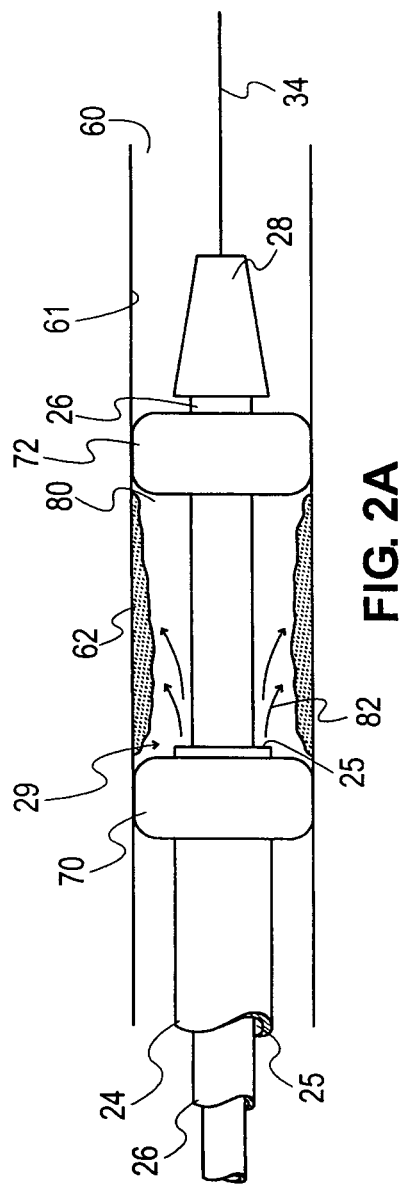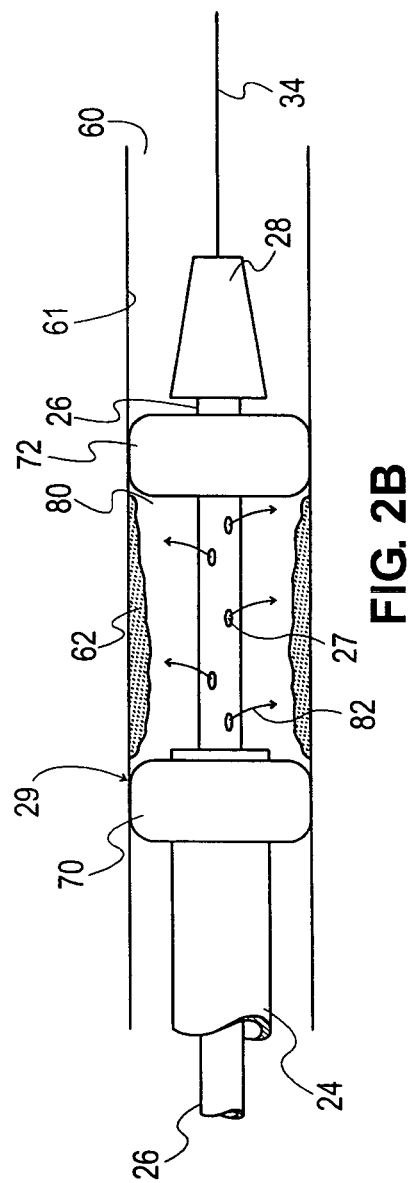

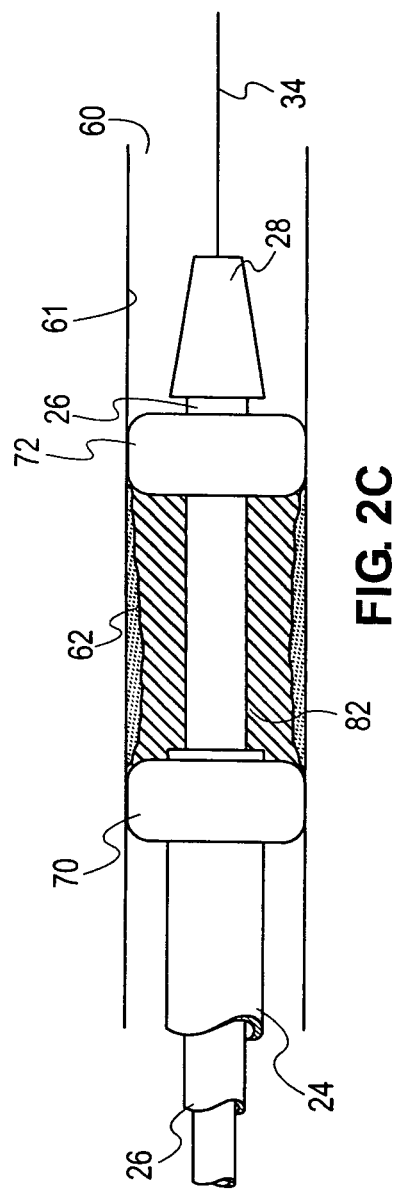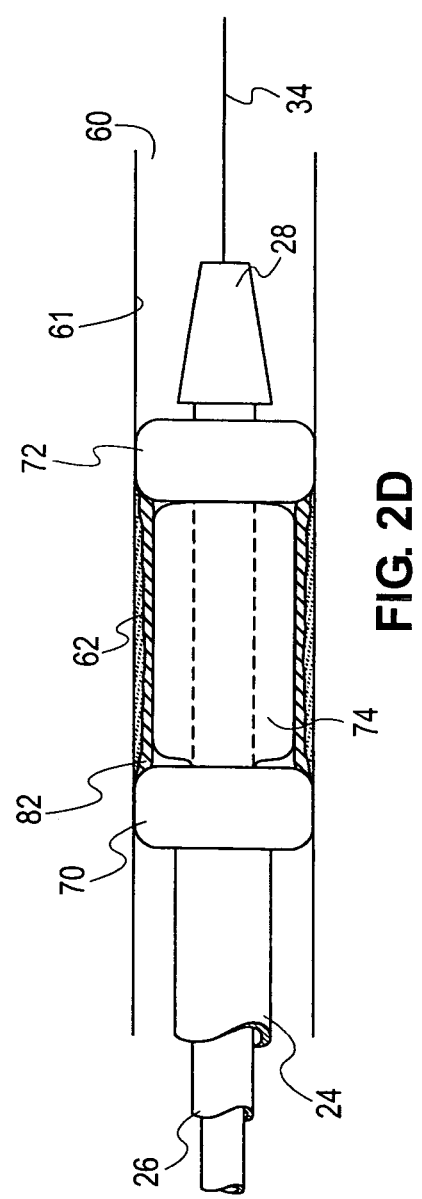

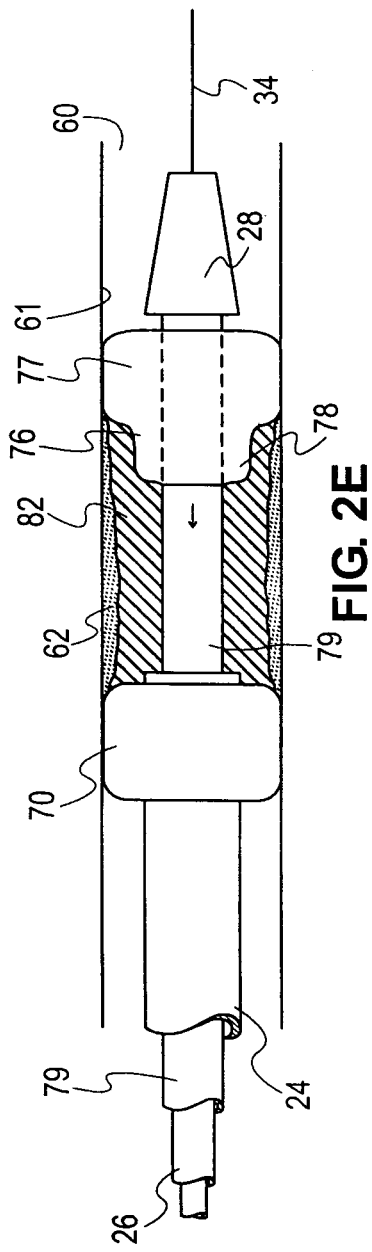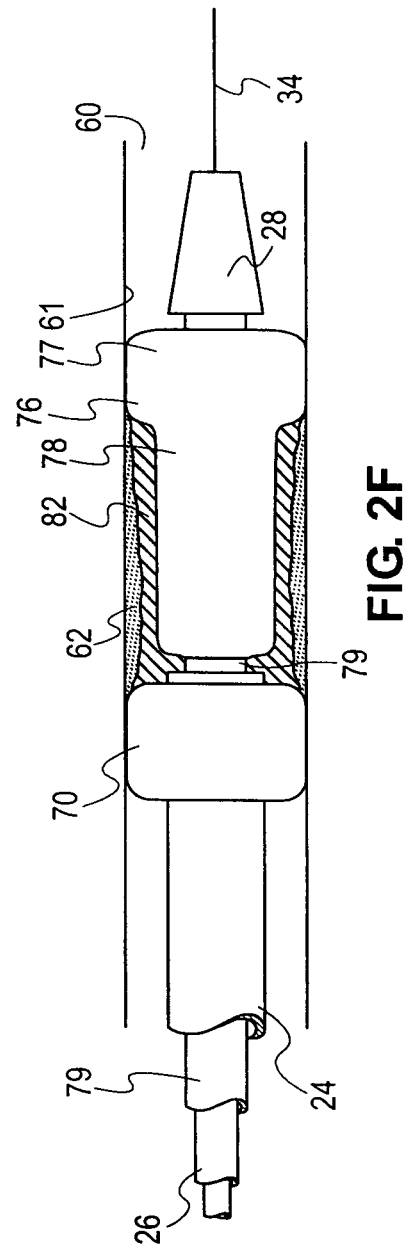

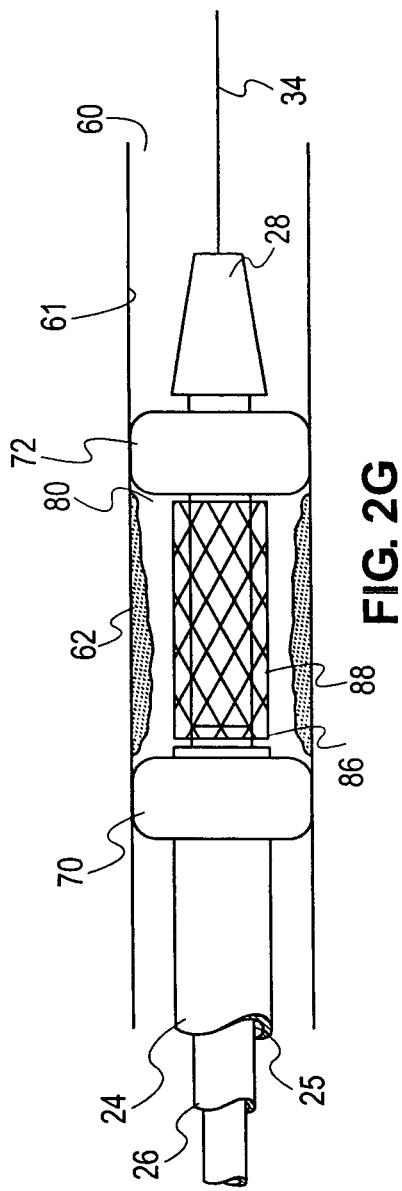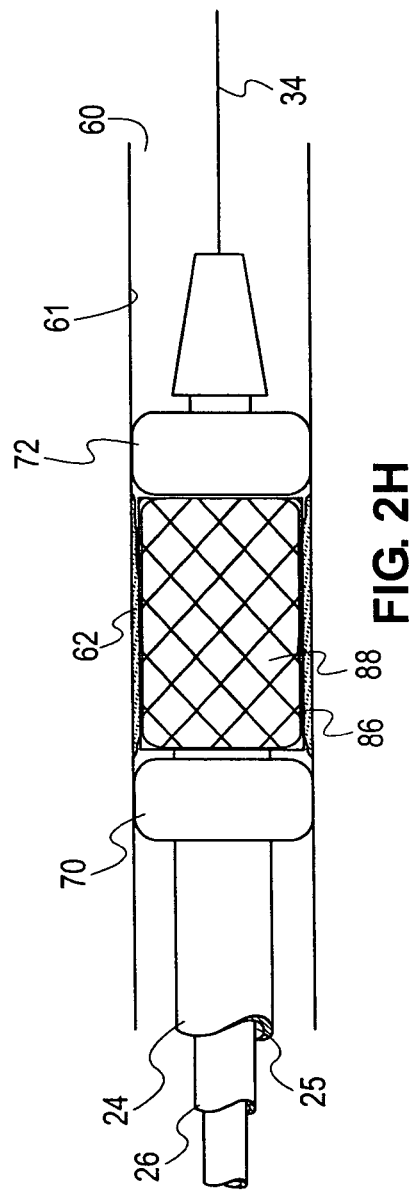

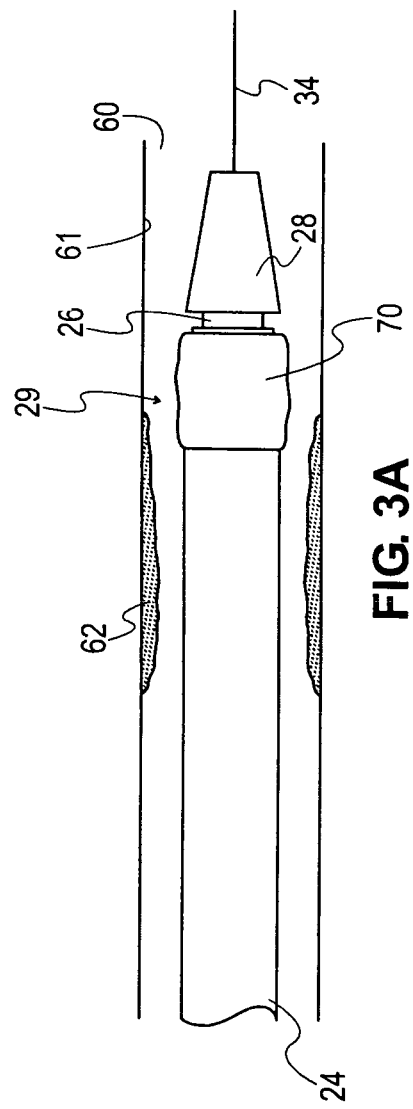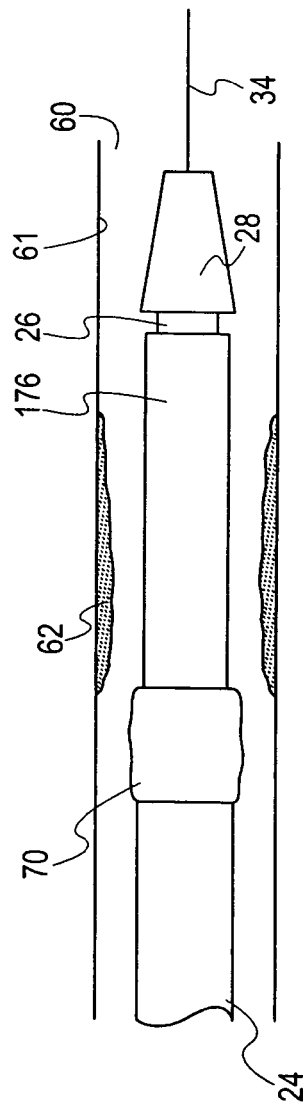
FIG. 3A
FIG. 3B

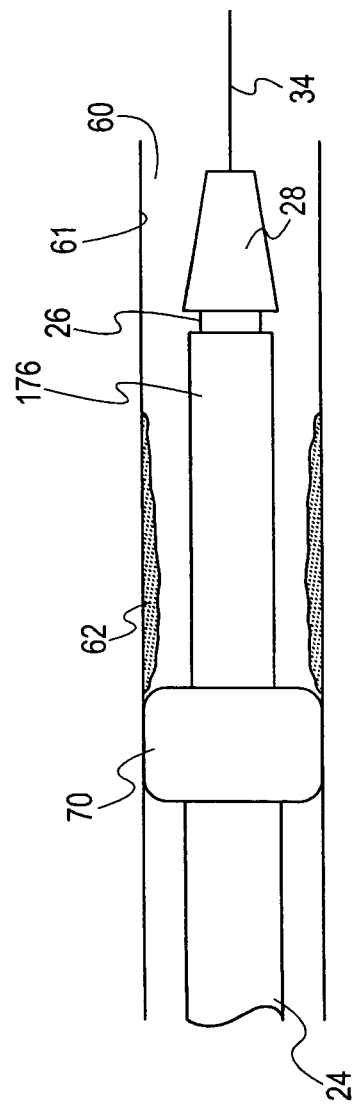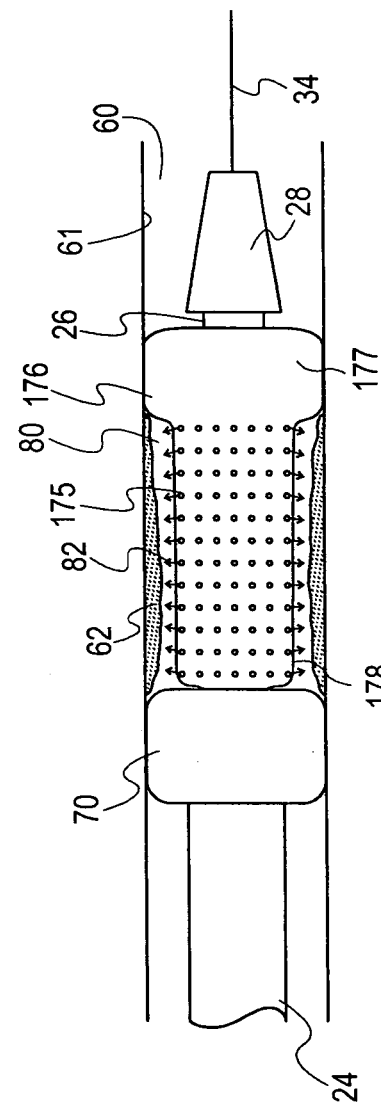

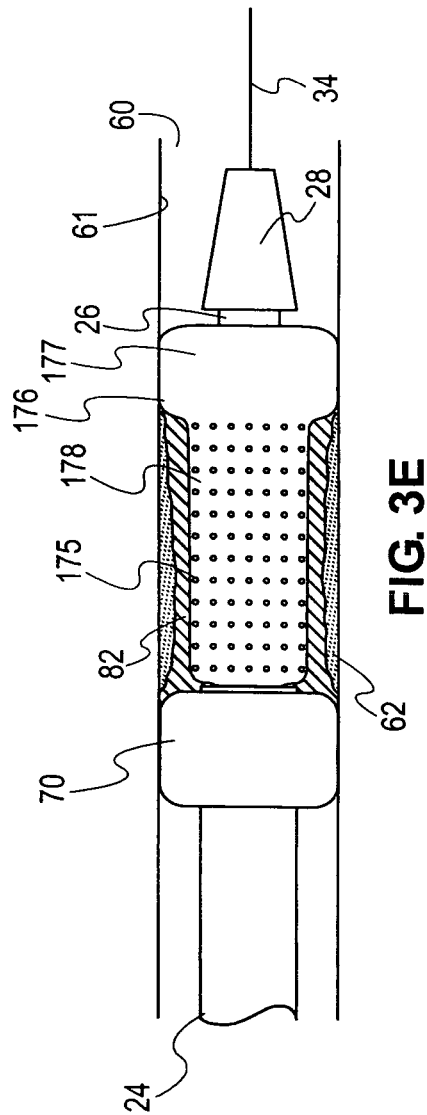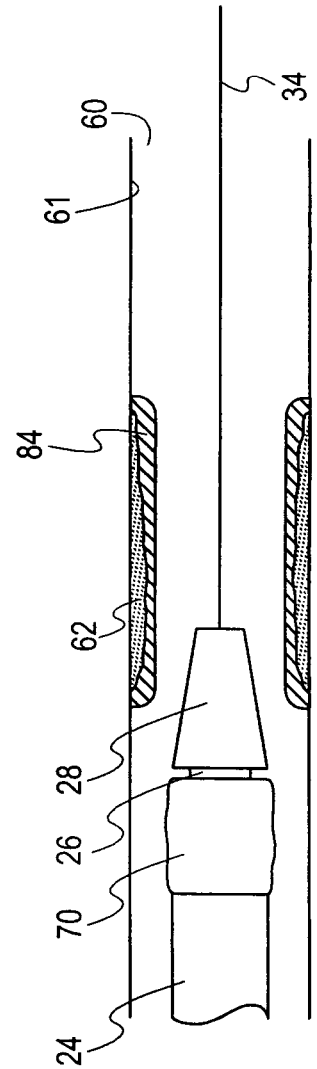

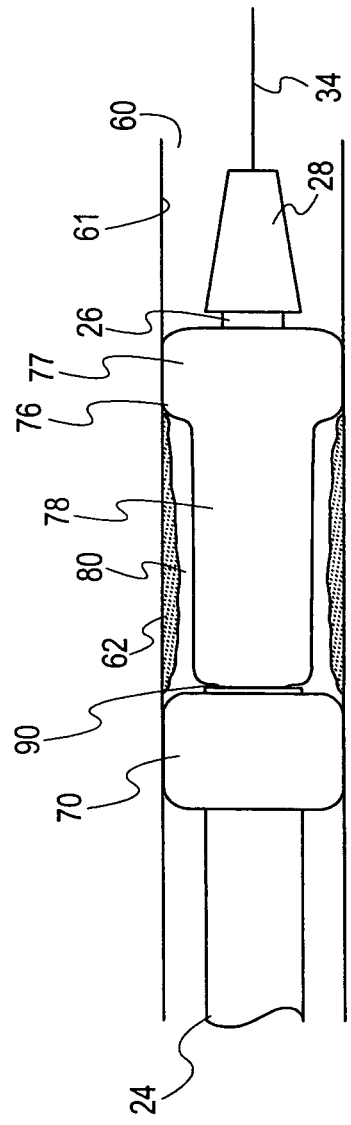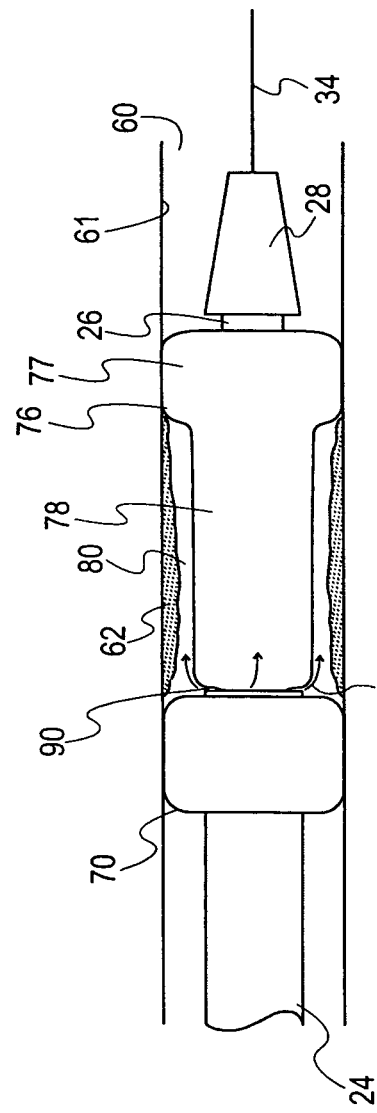

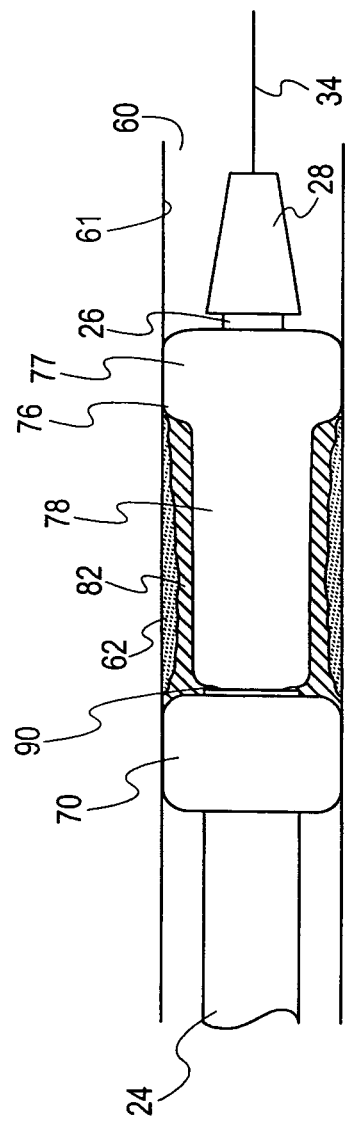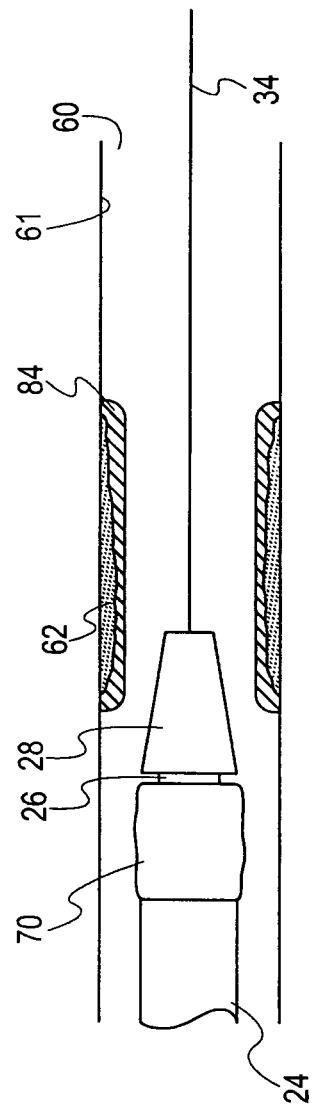

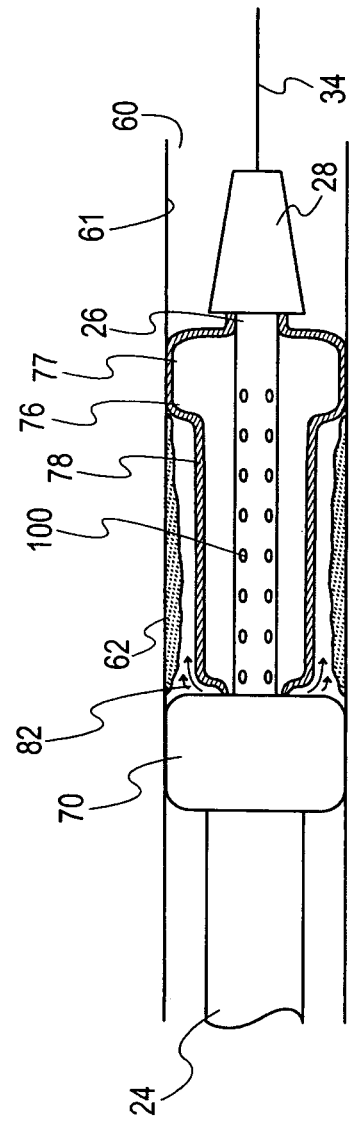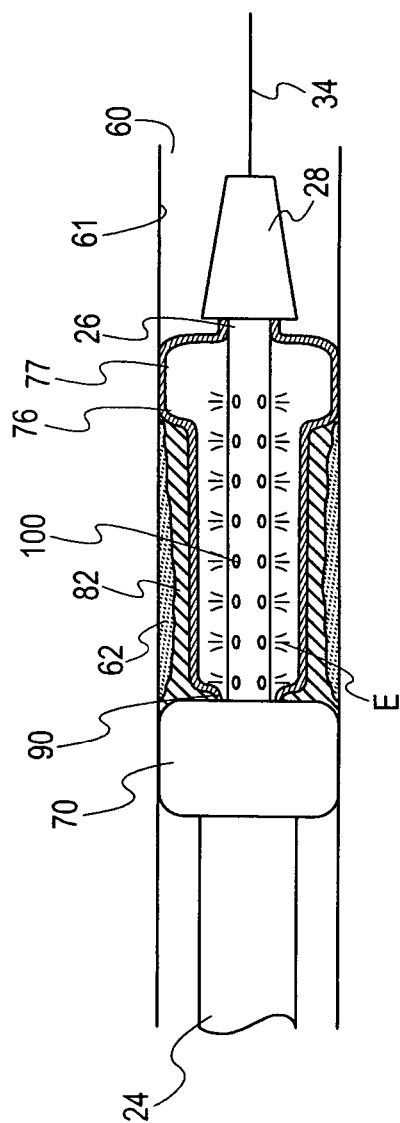

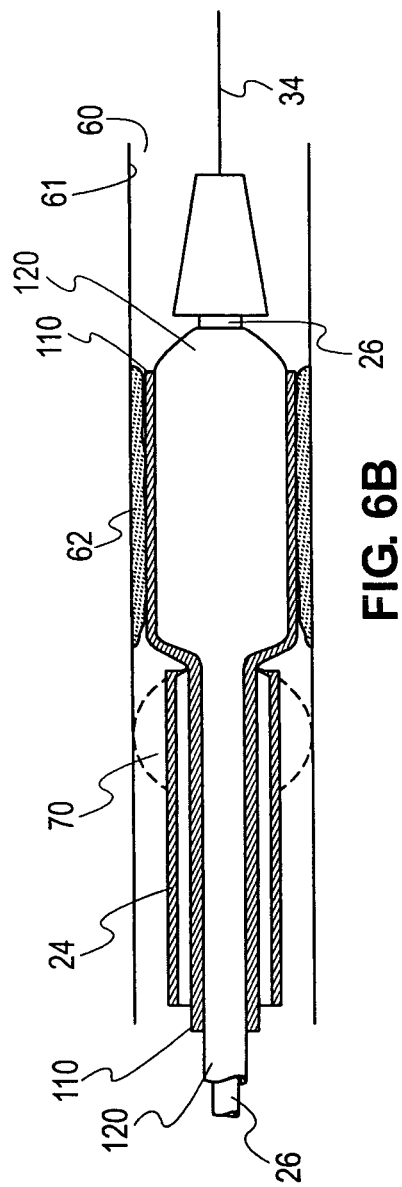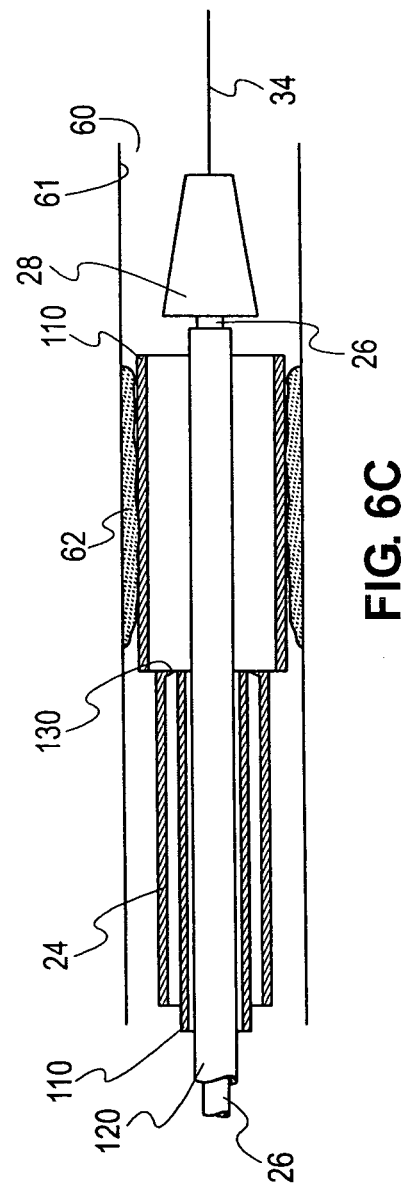

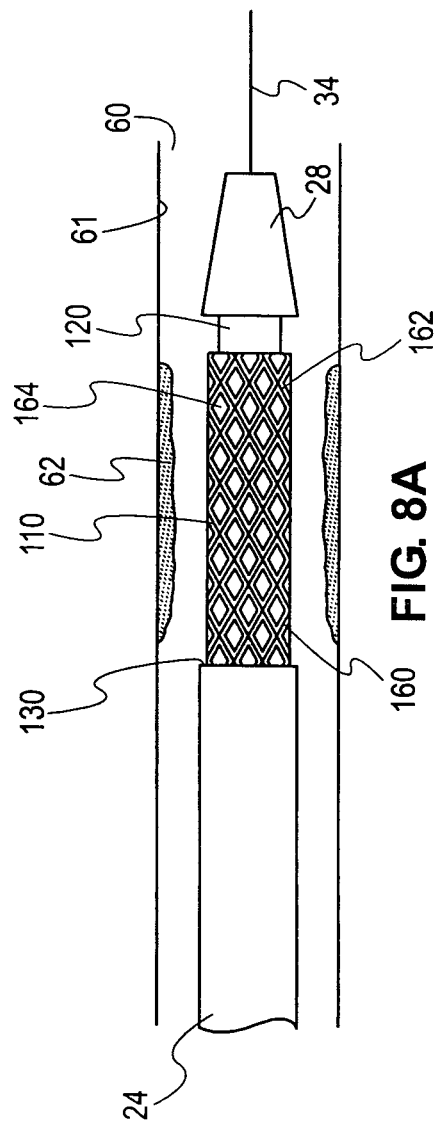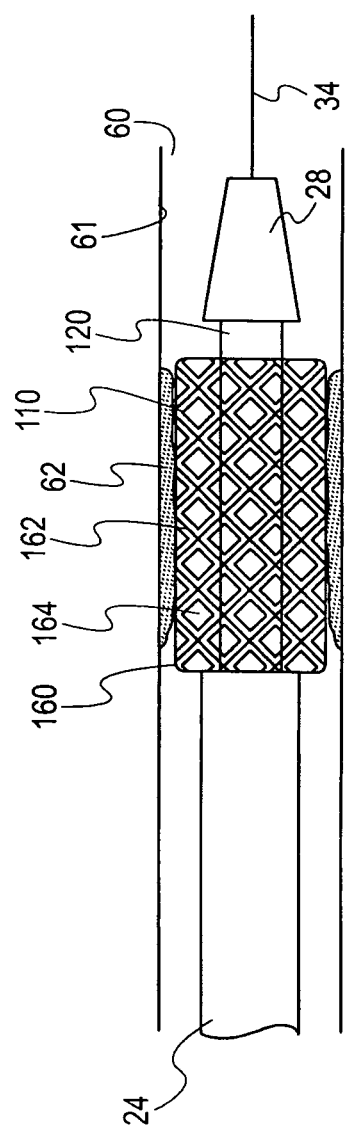
FIG. 8A
FIG. 8B

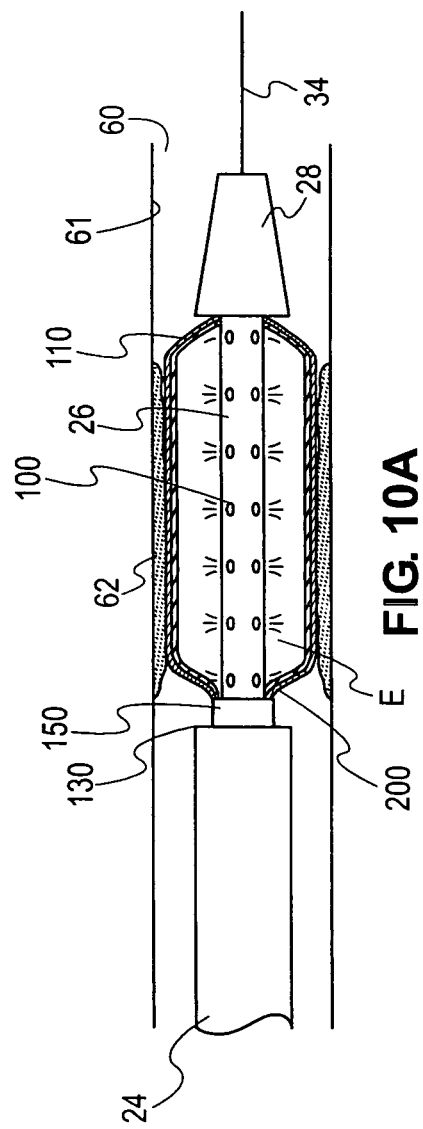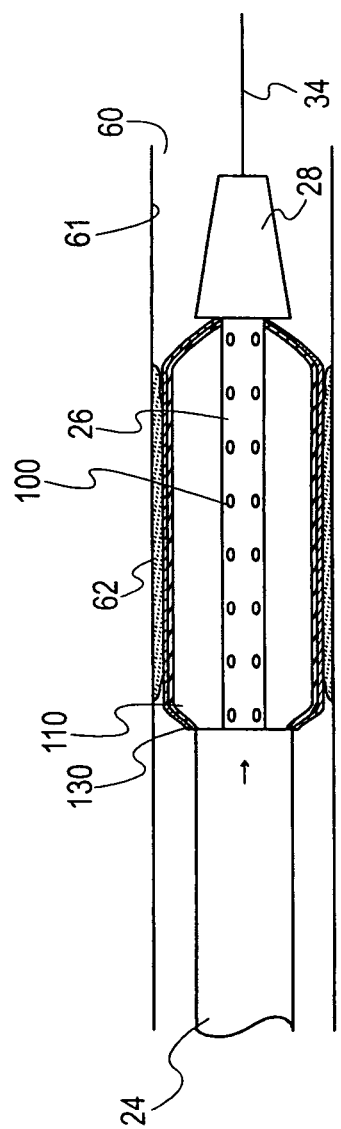

IN SITU STENT FORMATION

BACKGROUND OF THE INVENTION

1. Field of the Invention

The present invention relates generally to medical devices and methods. More particularly, the present invention relates to apparatus and methods for in situ formation of luminal prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or, even if survived, can cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that the coating of stents using anti-proliferative drugs, such as paclitaxel, can significantly reduce the occurrence of hyperplasia in angioplasty treated coronary arteries which have been stented with the coated stents. Stents are also used to treat blockages of peripheral blood vessels, including those in the neck, head, abdomen and legs.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the use of multiple stent delivery catheters. Moreover, it can be difficult to stent an angioplasty-treated region of a blood vessel with the optimum stent length.

For these reasons, it would be desirable to provide improved stents, stent forming apparatus and methods, stent delivery systems, stenting methods, and the like, for the treatment of patients having coronary artery disease, as well as other occlusive diseases of the vasculature and other anatomical structures. In particular, it would be desirable to provide stents, stent forming apparatus and methods, stent delivery systems, and methods for the treatment of disseminated and variable length stenotic regions within the vasculature. For example, it would be desirable to provide a practical method which permits a physician to tailor the length of the stent delivered to a treatment location while the delivery apparatus is adjacent to the treatment location, rather than having to deliver a stent having a predetermined length. More specifically, it would be desirable to provide apparatus, systems, and methods for facilitating the delivery and in situ formation of stents and other prostheses to blood vessels or other target body lumens. Such apparatus, systems, and methods should be suitable for delivery and in situ formation of individual stents or prostheses having lengths ranging from very short (typically as short as 3 mm or shorter) to relatively long (typically as long as 100 mm or longer), which lengths may be determined for a subject stent during the course of the stent delivery and in situ formation. Such apparatus, systems, and methods should also be capable of delivering and forming multiple individual stents at multiple treatment locations during a single interventional procedure (i.e., without fully withdrawing the catheter from the patient). At least some of these objectives, and others, will be met by the inventions described hereinafter.

2. Description of the Background Art

U.S. Pat. No. 6,258,117 B1 describes a stent having multiple sections connected by separable or frangible connecting regions. Optionally, the connecting regions are severed after the stent structure has been implanted in the blood vessel. U.S. Pat. Nos. 5,571,086; 5,776,141; and 6,143,016 describe an expandable sleeve for placement over a balloon catheter for the delivery of one or two stent structures to the vasculature. U.S. Pat. No. 5,697,948 describes a catheter for delivering stents covered by a sheath.

U.S. Pat. No. 5,059,211 describes an expandable absorbable stent. U.S. Pat. No. 5,147,385 describes methods for using stents that are hollow, cylindrical structures made of synthetic substance that becomes plastic and malleable in a temperature range of from 45° to 75° Celsius. U.S. Pat. Nos. 5,213,580 and 5,947,977 describe processes for paving or sealing interior surfaces of body vessels or organs by entering the interior of the vessel or organ and applying a polymer to the interior surfaces thereof. U.S. Pat. No. 5,670,161 describes an expandable, biodegradable stent. U.S. Pat. No. 6,607,553 describes an expandable stent that is coated with a radiation-absorbing material. U.S. Pat. No. 6,039,757 describes a fenestrated stent formed in a body lumen. U.S. Pat. No. 6,623,519 describes an endoluminal stent containing a hollow passageway for circulating fluids to treat vascular walls affected with malignant growths or experiencing restenosis.

BRIEF SUMMARY OF THE INVENTION

The present invention provides methods and apparatus for deploying a prosthesis in a lumen. The methods and apparatus are particularly adapted for use in stenting of body lumens, and more typically stenting coronary arteries. The methods and apparatus will also find significant use in the peripheral vasculature, the cerebral vasculature, and in other ducts, such as the biliary duct, the fallopian tubes, and the like. The terms "stent" and "stenting" are defined to include any of the wide variety of prostheses and scaffolds that are designed to be intraluminally introduced to a treatment site to apply a radially outward force against the inner wall of the body lumen at that site. The terms "prosthesis" and "prostheses" refer broadly to all stents and other scaffold-like structures that are intended for deployment within body lumens.

In one aspect of the invention, an apparatus is provided for deploying one or more prostheses into a target body lumen by isolating a target region of the lumen, introducing a fluidized prosthesis material into the isolated region, shaping the fluidized material, and then allowing or causing the material to harden into a suitable prosthesis. The apparatus comprises a flexible catheter having proximal and distal ends. The catheter may include a plurality of generally cylindrical shafts that are capable of sliding independently of one another, and one or more lumens that may provide fluid communication between components located at the proximal and distal ends of the catheter. The catheter may also include a distal tip, preferably having a profile to reduce or eliminate the occurrence of trauma due to contact of the body lumen by the tip.

A control member, such as a handle, may be provided to provide the capability of manipulating the plurality of catheter shafts and other catheter components. The control member may include one or more sliders, knobs, actuators, or other control members that are coupled to the plurality of catheter shafts and other catheter components to perform the manipulation functions. The control member may also provide ports or other connectivity mechanisms suitable for providing various fluid or other media to the lumens provided in the catheter. The fluids and other media may include inflation media for expansion members (e.g., balloons) located on the distal portion of the catheter, heating or cooling media, or fluidized prosthetic material for delivery to a treatment location.

A guidewire tube extends through at least a portion of the catheter and terminates at a distal exit port at the distal end of the catheter. In one embodiment, for use in over-the-wire applications, the guidewire tube extends over the entire length of the catheter and has a proximal exit port at the proximal end of the catheter. In another embodiment, for use in rapid exchange applications, the guidewire tube extends through the distal end of the catheter and has a proximal exit port closer to the distal end of the catheter than to the proximal end, and preferably about 20-35 cm from the distal end of the catheter. In this latter embodiment, the proximal exit port may be cut into the sidewall of one or more of the catheter shafts to face laterally, or alternatively oriented so as to face generally in a proximal direction. One or both of the guidewire tube exit ports may be fluid sealed or fluid sealable so as to limit the introduction of blood or other fluids through the guidewire tube. Usually the guidewire tube is fixed relative to at least one of the catheter shafts and may be attached thereto.

The distal end of the catheter is provided with a mechanism for forming a prosthesis at a target location within the body lumen. The prosthesis forming mechanism typically comprises a proximal isolation member and a distal isolation member, each of which is selectively and independently expandable. Each of the proximal and distal expandable isolation members is fixed relative to at least one of the catheter shafts, thereby providing the capability of changing the position of one of the expandable isolation members with respect to the other. For example, in one embodiment, the proximal expandable isolation member is fixed to an outer shaft of the catheter, and the distal expandable isolation member is fixed to an inner shaft of the catheter. The outer shaft is slidable proximally relative to the inner shaft to provide the capability of moving the proximal expandable isolation member proximally relative to the distal expandable isolation member, thereby changing the longitudinal distance between the two expandable isolation members.

The distal end of the catheter is also provided with an exit port of a fluid delivery member that is suitable for delivering a fluid material to be formed into a prosthesis. The fluid delivery member is typically a passage provided in the catheter. The fluid delivery member may comprise a lumen, an annular passage, or another type of passage extending proximally from the exit port to a proximal port on the proximal end of the catheter or directly to a fluid source. The exit port of the fluid delivery member typically opens into a space located between the distal and proximal expandable isolation members. In one embodiment, the exit port is a single port at the terminal end of a lumen serving as the fluid delivery member. In another embodiment, the exit port is an annular port at the terminal end of an annular passage serving as the fluid delivery member. In yet another embodiment, the exit port may be formed as one or more exit holes formed in an internal catheter shaft, an expandable balloon, or other catheter structure located between the proximal and distal expandable isolation members.

The distal end of the catheter may also be provided with a prosthesis molding member, such as a selectively expandable balloon. Typically, the prosthesis molding member will be fixed to an inner catheter shaft and will be located between the proximal and distal expandable isolation members. In several embodiments, the prosthesis molding member may be formed integrally with one or both of the proximal and distal expandable isolation members. The length of the prosthesis molding member is preferably dependent upon the distance that the outer catheter shaft is withdrawn relative to the inner catheter shaft upon which the prosthesis molding member is fixed. The prosthesis forming member preferably has a shape and size that is adapted to form the prosthesis as and after the fluid material is delivered. For example, the prosthesis forming member may have a cross-sectional profile having an hourglass, tapered, stepped, barrel-shaped, or other shape suitable for forming the prosthesis within a body lumen.

In several embodiments, the distal end of the catheter may also be provided with a mechanism for curing the prosthesis material after its delivery to aid in the formation of the prosthesis. Typically, the curing mechanism comprises an emitter for delivering energy, such as ultraviolet (UV), infrared (IR), radio frequency (RF), microwave (MW), laser, or other suitable form of energy. The energy is typically directed radially from the emitter outward to encounter the prosthetic material to promote curing of the material.

In another aspect of the invention, a method of delivering a prosthesis in a target vessel of a patient comprises introducing a distal portion of a catheter through the patient's vasculature to the target vessel, isolating a void space between the distal end of the catheter and a surface of the target vessel, introducing a liquid prosthetic material into the void space, then forming the liquid prosthetic material into a molded shape to form a prosthesis.

The step of creating a void space at a target site within the vessel may include inflating a proximal isolation balloon fixed to the outer shaft, inflating a distal isolation balloon fixed to the internal shaft, and inflating a molding balloon fixed to the internal shaft between the proximal and distal isolation balloons. The isolation balloons and molding balloon cooperate with the internal surface of the vessel to create a tubular void space. The relative positions of the isolation balloons may be adjusted in order to adjust the length and size of the tubular void space, thereby providing the ability to form a prosthesis of a selected, adjustable length. A fluidized prosthesis material may then be introduced into the void space, such as by injecting through a delivery lumen provided in the delivery catheter. The delivery lumen may be provided with one or more exit ports located in the void space. After the fluidized prosthesis material is introduced into the void space, it is allowed to harden or caused to harden, such as by exposing the material to a curing mechanism.

In another aspect of the invention, an apparatus is provided for deploying one or more prostheses into a target body lumen by advancing a distal end of a delivery device to a body lumen treatment site, exposing a desired length of prosthetic material in pliable form, conforming the pliable prosthetic material to its deployment shape, and then allowing or causing the pliable prosthetic material to harden into a suitable prosthesis. The apparatus comprises a flexible catheter having proximal and distal ends. The catheter may include a plurality of generally cylindrical shafts that are capable of sliding independently of one another, and one or more lumens that may provide fluid communication between components located at the proximal and distal ends of the catheter. The catheter may also include a distal tip, preferably having a profile to reduce or eliminate the occurrence of trauma due to contact of the body lumen by the tip.

The distal end of the catheter is provided with a mechanism for creating a tubular prosthesis of a selectable length at a target site within the body lumen. The mechanism includes an outer sheath that may be retracted to expose a selectable length of a pliable, flexible pre-stent member. As used herein, the term "pre-stent member" means a generally tubular body that is flexible and pliable such that it may be expanded from a first diameter small enough to be housed within the delivery catheter to a second diameter large enough to conform to the internal surface of a target vessel or organ. The pre-stent member comprises a material that is capable of transforming (or being transformed) from a first pliable, flexible state suitable for delivery by the catheter to a second more rigid state suitable for performing a scaffolding function within the target vessel or organ. The flexible pre-stent member then expands, or is expanded by the user, to conform to the interior of the lumen. The pre-stent member then hardens, or is caused to harden, to form a resilient prosthesis with sufficient radial strength to provide a scaffold.

In one embodiment, the flexible pre-stent member comprises a tube-shaped length of material that extends proximally from near the distal end of the catheter beneath the outer sheath. Preferably, a variable length expandable member is provided, such as an inflatable balloon, which also extends proximally from near the distal end of the catheter beneath the pre-stent member. When the outer sheath is withdrawn, it exposes a selected length of the flexible pre-stent member and the underlying expandable member. The expandable member may then be expanded to cause the exposed length of flexible pre-stent member to conform to the interior of the body lumen.

The length of the expandable member is preferably controlled by the distance the outer sheath is retracted. For example, the outer sheath may be a fiber-reinforced shaft that is capable of preventing or substantially inhibiting those portions of the expandable member that are covered by the outer sheath from expanding when the remainder of the expandable member is caused to expand. Alternatively, a separate restraining member, such as another catheter shaft, may be provided to allow selective expansion of the expandable member.

A cutting device may be provided near the distal end of the outer sheath, either formed as part of the distal end of the outer sheath or as a separate member. The cutting device may comprise a mechanical cutter such as a cutting blade, a heating element, an electrode, an electrolytic cutter, an ultrasonic cutter, a chemical cutter, or any other form of cutting device suitable for creating a separation in the flexible pre-stent member. Preferably, the cutting device is also capable of sealing the cut portion of the prosthesis material when such sealing is necessary or desired. A separate expandable isolation member, such as another inflatable balloon, may be provided near the distal end of the outer sheath but proximal to the cutting device.

In another embodiment, the pre-stent member may be provided as an inflatable member, such as a cylindrical tubular member having an annular fluid lumen, a coil-shaped tubular member in which the coil has a fluid lumen, a tubular lattice having a fluid lumen, or other similar structure. In this embodiment, the deployed pre-stent member may be expanded by an inflation member such as the one described above, or it may be expanded by inflating the lumen contained in the body of the flexible pre-stent member after it has been exposed by retracting the outer sheath, or a combination of both. The material used to inflate the pre-stent member may comprise fluidized prosthesis material, a hardening agent, a filler, or some other material. In a particularly preferred form, the inflation medium may include a drug that is able to elute through porous walls of the prosthesis.

The inflatable pre-stent member may be free from attachment to the catheter at its distal end, or it may be attached to an inner shaft, the distal tip, or some other catheter component at its distal end. If the distal end of the pre-stent member is free from attachment, it is preferably sealed to facilitate inflation of the prosthesis. If the distal end of the pre-stent member is attached to the catheter at its distal end, it may also be cut from the catheter by the cutting device by advancing the cutting device distally after the proximal portion of the pre-stent member is cut. Optionally, after cutting, the cutting device will seal the ends of the pre-stent member.

In several of the foregoing embodiments, the distal end of the catheter may also be provided with a mechanism for curing the pre-stent member after its delivery to aid in the formation of the prosthesis. Typically, the curing mechanism comprises an emitter for delivering energy, such as ultraviolet (UV), infrared (IR), radio frequency (RF), microwave (MW), laser, or other suitable form of energy. The energy is typically directed radially from the emitter outward to encounter the pre-stent member to promote curing of the material.

In another aspect of the invention, a method of delivering a prosthesis in a target vessel of a patient comprises inserting a guidewire through the patient's vasculature to the target vessel; slidably coupling a delivery catheter to the guidewire, the delivery catheter having an outer shaft, a flexible tubular pre-stent member of a prosthesis material, and a cutting device, the guidewire being slidably positioned through a guidewire tube; advancing the delivery catheter over the guidewire to the target vessel; retracting the outer shaft relative to the tubular pre-stent member; expanding or causing to expand the flexible pre-stent member; and allowing or causing the flexible pre-stent member material to harden.

The prostheses formed using the apparatus and methods described herein are particularly suitable for use as stents, and particularly stents for use in the coronary arteries. The stents may be formed of any of a number of known materials suitable for use, including several known polymers, metals, ceramics, proteins, or other materials that may be used in fluid form at room temperature and/or body temperature and that may be cured or hardened and remain sufficiently resilient while in contact with blood or other bodily fluids. Examples of polymers that may be used in the prostheses described herein are bioabsorbable or biocompatible polymers such as poly(lactide) (PLA), poly(glycolic acid) (PGA), poly(lactide-co-glycolide) (PLGA), and other polyhydroxyacids, polyethylene glycol (PEG), poly(caprolactone), polycarbonates, polyamides, polyanhydrides, polyamino acids, poly-ortho esters, polyacetals, degradable polycyanoacrylates and degradable polyurethanes. Various hardenable materials including 2-part epoxies, polyurethanes and other materials suitable for use with the invention are described in U.S. Pat. No. 6,875,212, which is incorporated herein by reference. Various other hardenable materials including compounds of proteins and polymers suitable for use with the invention are described in U.S. Pat. No. 6,371,975, which is incorporated herein by reference. Still other hardenable materials including compounds having an electrophilic polymer material and a nucleophilic polymer material in a buffer material suitable for use with the invention are described in U.S. Pat. No. 6,830,756, which is incorporated herein by reference.

Examples of natural polymers and materials include proteins such as albumin, collagen, fibrin, fibrinogen, hydroxyapatite (HAp), and synthetic polyamino acids, and polysaccharides such as alginate, heparin, and other naturally occurring biodegradable polymers of sugar units. Additional suitable materials are also described in, for example, U.S. Pat. Nos. 5,059,211, 5,085,629, 5,147,385, 5,213,580, 5,670,161, 5,749,922, 5,947,977, 6,039,757, 6,607,553, and 6,623,519, each of which is incorporated herein by reference. Composites comprising any of the above materials combined with other biocompatible materials including metals, ceramics, carbon materials, and plastics may also be used to produce the desired strength, flexibility, elution, and bioerosion characteristics. Further, any of these materials may be used in combination with scaffolds, braids, or other strengthening materials, including woven metals or polymers, textile fabrics, metal or carbon fibers, and the like. In addition, these materials may be mixed not only with active therapeutic agents as described elsewhere herein, but with materials to enhance visibility via fluoroscopy, ultrasound, or magnetic resonance imaging. For example, fillers of radiopaque powders such as platinum, tantalum, tungsten, iridium, or gold may be combined with the materials above.

The finished prosthesis is preferably sufficiently resilient and/or radially rigid to perform the scaffolding function within the target vessel. The degree of strength and flexibility required will vary depending, at least in part, on the vessel environment and the intended use. Typically, the prosthesis will be hardened, by which it is meant that the material has sufficient structural strength to provide the outward radial forces required to at least temporarily scaffold the vessel and maintain its patency. However, the hardened material will desirably have flexibility to allow the prosthesis to assume curved and other non-linear shapes to conform to the natural shape of the vessel and the movement of the vessel (e.g., as the heart beats). The prosthesis material may harden after the passage of seconds or minutes, or it may be cured using separate means, as discussed above and elsewhere herein. For example, the material may be hardened by adding a hardening agent in situ (similar to a 2-part epoxy). The material may alternatively be cured by radiating it with energy such as UV or IR light, ultrasound, or RF energy emitted by the delivery catheter itself or by an external source (outside the vessel or outside the body). The stent material could alternatively be cured by heating or cooling via a heating or cooling element on the catheter, or by delivering a warm or cool liquid such as saline through the catheter into the isolated space where the stent is formed.

The prosthesis material may optionally be biodegradable so as to be eventually absorbed or expelled by the body. In many applications such as coronary stenting, the stent need perform a scaffolding function for only 30-60 days following placement to allow the drug to elute into the vessel, after which complete biodegradation of the stent is acceptable.

The prostheses described herein may also be combined or used in conjunction with other stent structures. For example, the prostheses described herein may be formed and delivered to a treatment location already having a metallic or other stent, or simultaneously with another metallic or other stent, in order to provide additional scaffolding, to deliver therapeutic materials contained on or in the prosthesis, or other functions. In several embodiments, a biodegradable material may be used to form a prosthesis that is used in conjunction with a metallic or other stent that has been previously deployed or that is deployed simultaneously with the prosthesis. The prosthesis and the metallic or other stent may be deployed from separate delivery devices or, preferably, from a single delivery catheter. In several embodiments, the metallic or other stent and the prosthesis are formed from materials that biodegrade at different rates, while in other embodiments the prosthesis and the metallic or other stent are formed from materials that biodegrade at the same or substantially similar rates. The user is thereby able to select combinations of materials to obtain desired results.

In each of the embodiments described herein, the prosthesis material may be combined with a drug or other therapeutic agent that inhibits restenosis, reduces thrombus formation or has other therapeutic effects. The drug or agent may be mixed with the prosthesis material and introduced with it to form the prosthesis, or the drug may be introduced into the isolated region separately from the prosthesis material, either simultaneously, before, or after introduction of the prosthesis material. For example, the prosthesis material and drug could be introduced in an alternating fashion so that the prosthesis has a sandwich structure with separate layers of drug and prosthesis material. Examples of drugs that may be included in the foregoing structures include taxol, rapamycin, analogs of rapamycin such as Everolimus, Biolimus A9, or ABT 578, thrombolytics such as heparin, as well as VEGF, gene therapy agents, and a range of other agents known to those of ordinary skill in the art.

BRIEF DESCRIPTION OF THE DRAWINGS

FIG. 2A is a side view, shown in partial cross-section, of an embodiment of a distal portion of a stent delivery catheter.

FIG. 2B is a side view, shown in partial cross-section, of another embodiment of a distal portion of a stent delivery catheter.

FIG. 2C is a side view, shown in partial cross-section, of the device shown in either of FIG. 2A or 2B.

FIG. 2D is a side view, shown in partial cross-section, of the device shown in either of FIG. 2A or 2B.

FIG. 2E is a side view, shown in partial cross-section, of another embodiment of a distal portion of a stent delivery catheter.

FIG. 2F is a side view, shown in partial cross-section, of the device shown in FIG. 2E.

FIG. 2G is a side view, shown in partial cross-section, of another embodiment of a distal portion of a stent delivery catheter.

FIG. 2H is a side view, shown in partial cross-section, of the device shown in FIG. 2G.

FIG. 2I is another side view, shown in partial cross-section, of the device shown in FIG. 2G.

FIG. 3A is a side view, shown in partial cross-section, of another embodiment of a distal portion of a stent delivery catheter.

FIG. 3B is a side view, shown in partial cross-section, of the device shown in FIG. 3A with the outer sheath retracted.

FIG. 3C is a side view, shown in partial cross-section, of the device shown in FIG. 3A, with the proximal isolation balloon expanded.

FIG. 3D is a side view, shown in partial cross-section, of the device shown in FIG. 3A, with the distal balloon expanded.

FIG. 3E is a side view, shown in partial cross-section, of the device shown in FIG. 3A, with the fluid stent material delivered.

FIG. 3F is a side view, shown in partial cross-section, of the device shown in FIG. 3A, being withdrawn from the treatment location.

FIG. 4A is a side view of another embodiment of a distal portion of a stent delivery catheter.

FIG. 4B is a side view of the device shown in FIG. 4A illustrating injection of fluid stent material.

FIG. 4C is a side view of the device shown in FIG. 4A illustrating molding of the fluid stent material.

FIG. 4D is a side view of the device shown in FIG. 4A, being withdrawn from the treatment location.

FIG. 5A is a side view, shown in partial cross-section, of another embodiment of a distal portion of a stent delivery catheter.

FIG. 5B is a side view, shown in partial cross-section, of the device shown in FIG. 5A, with an illustration of exposure to a curing mechanism.

FIG. 6B is a side view, shown in partial cross-section, of the device shown in FIG. 6A, with an illustration of expansion of a pre-stent member.

FIG. 6C is a side view, shown in partial cross-section, of the device shown in FIG. 6A, after shearing of a pre-stent member.

FIG. 8A is a side view of another embodiment of a distal portion of a stent delivery catheter.

FIG. 8B is a side view of the device shown in FIG. 8A, illustrating expansion of a pre-stent member.

FIG. 10A is a side view, shown in partial cross-section, of another embodiment of a distal portion of a stent delivery catheter.

FIG. 10B is a side view, shown in partial cross-section, of the device shown in FIG. 10A, illustrating shearing of the proximal end of the pre-stent member.

DETAILED DESCRIPTION OF THE PREFERRED EMBODIMENTS

Xtent, Inc., assignee of the present application, is also the assignee of U.S. patent application Ser. No. 10/306,813, filed Nov. 27, 2002, entitled "Apparatus and Methods for Delivery of Multiple Distributed Stents" ("the '813 application"), and U.S. patent application Ser. No. 10/637,713, filed Aug. 8, 2003, entitled "Apparatus and Methods for Deployment of Vascular Prostheses" ("the '713 application"). Each of the foregoing applications is hereby incorporated by reference in its entirety.

Figure 1:
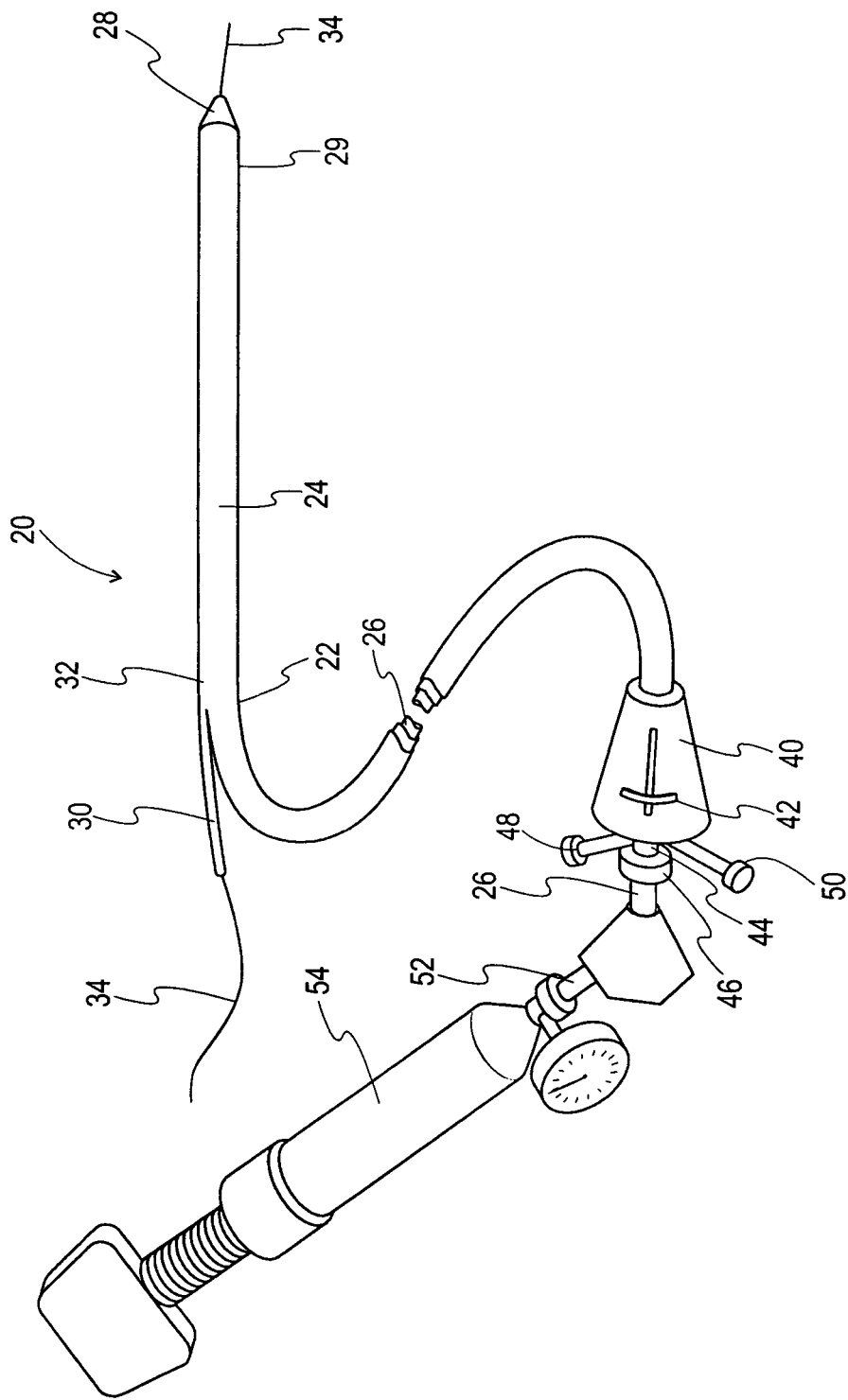
FIG. 1 is a perspective view of a stent delivery catheter.
Figure 21:
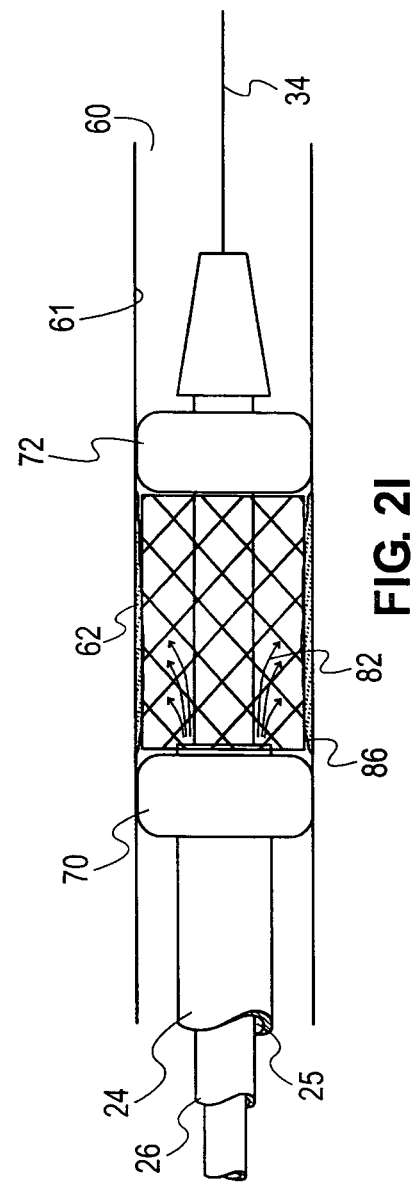

A first embodiment of a prosthesis forming and deploying apparatus is illustrated in FIG. 1. A stent delivery catheter 20 includes a catheter body 22 comprising an outer sheath 24 slidably disposed over an inner shaft 26. A tapered nosecone 28 composed of a soft elastomeric material to reduce trauma to the vessel during advancement of the device, is fixed to the distal end 29 of the catheter 20. A guidewire tube 30 is slidably positioned through a guidewire tube exit port 32 in the outer sheath 24 at a proximal distance from the distal end 29 of the catheter. A guidewire 34 is positioned slidably through the guidewire tube 30, the distal end 29 of the catheter, and the nosecone 28 and extends distally thereof.

A handle 40 is attached to a proximal end of the outer sheath 24 and includes an actuator 42 slidably mounted thereto for purposes described below. An adaptor 44 is mounted to the proximal end of the handle 40 and provides a catheter port 46 through which the inner shaft 26 is slidably positioned. A first fluid introduction port 48 is mounted to the side of the adaptor 44 through which a fluid may be delivered through the catheter body to the distal portion of the catheter. A second fluid introduction port 50 is also mounted to the side of the adaptor 44 through which another fluid (or the same fluid) may be delivered to the distal portion of the catheter. In several embodiments described herein, the first fluid introduction port 48 is used to deliver a fluidized stent material (described more fully below) to the distal portion of the catheter, and the second introduction port 50 is used to deliver an inflation medium to an expandable member (such as a balloon) located on the distal portion of the catheter. An annular seal (not shown) in the catheter port seals around the inner shaft 26 to prevent fluid from leaking through the catheter port 46. Optionally, a clamp (also not shown) such as a threaded collar, can be mounted to the catheter port to lock the inner shaft relative to the handle.

The inner shaft 26 has a proximal end to which is mounted an inflation adaptor 52. The inflation adaptor 52 is configured to be fluidly coupled to an inflation device 54, which may be any commercially available balloon inflation device such as those sold under the trade name "Indeflator™," available from Advanced Cardiovascular Systems of Santa Clara, Calif. (Similarly, such an inflation device 54 may also be used to deliver an inflation medium through the second introduction port 52.) The inflation adaptor 52 may be placed in fluid communication with one or more expandable members (such as balloons) located at or near the distal end of the catheter via one or more inflation lumens to enable inflation of the one or more expandable members.

Those skilled in the art will recognize that the features on and functions performed by the handle 40 and its components may be modified or augmented in ways that are generally conventional in the art. For example, several embodiments of the delivery catheters described herein include multiple expandable members, such as inflation balloons, that have inflation lumens in fluid communication with the handle 40. Several embodiments of the delivery catheters described herein also include other lumens in fluid communication with the handle 40 for delivery of other fluid media, such as fluid stent material or heating or cooling media. Other embodiments include energy emitters in conductive communication with the handle 40. Persons of skill in the art will recognize that additional ports, inflation devices, fluid sources, energy sources, and other features may be included on or in association with the handle 40 illustrated in FIG. 1.

Referring now to FIGS. 2A-2I, a distal portion 29 of a stent delivery catheter 20 is shown in partial cross-section within the interior of a blood vessel 60 having a lesion 62. As shown in FIG. 2A, the outer sheath 24 has been retracted to expose a portion of the distal end of the inner shaft 26 proximal to the nosecone 28. A proximal isolation balloon 70 is fixed to the outer sheath 24 near its distal end. An inflation lumen (not shown) is provided in the outer sheath 24 extending from the proximal isolation balloon 70 to the proximal end of the outer sheath where it can be attached to a port and an inflation device to selectively expand or contract the proximal isolation balloon 70. Similarly, a distal isolation balloon 72 is fixed to the inner shaft 26 near its distal end. Another inflation lumen (not shown) is provided in the inner shaft 26 extending from the distal isolation balloon 72 to the proximal end of the inner shaft 26 where it can be attached to a port and an inflation device to selectively expand or contract the distal isolation balloon 72. Although each of the proximal and distal isolation balloons is shown in its expanded state, it will be understood that each of the isolation balloons may be contracted in order to more easily advance or retract the outer sheath 24 or the catheter 20.

Prior to inflating the proximal isolation balloon 70, the outer sheath 24 may be retracted over a range of distance relative to the inner shaft 26 by actuation of the actuator 42 on the handle 40. For example, in the preferred embodiment, the outer sheath 24 may be retracted over a range of distances from about 1 mm to about 100 mm. As shown more fully below, the amount of retraction of the outer sheath 24 relative to the inner shaft 26 will determine the length of a prosthesis to be formed by the delivery catheter 20. Thus, the adjustability of the distance that the outer sheath 24 may be retracted creates an ability by the user to form and deploy a stent having a desired length.

Once the outer sheath 24 has been retracted by a distance sufficient to form a stent of the desired length, the proximal isolation balloon 70 and distal isolation balloon 72 may be expanded. Expansion of the isolation balloons creates a void space 80 within the blood vessel 60 between the pair of isolation balloons. The void space 80 is defined, at least initially, by the isolation balloons 70, 72, the internal vessel wall 61, and the inner shaft 26 of the delivery catheter.

Once the void space 80 is created, a fluidized stent material 82 may be introduced into the void space 80. In the embodiment shown in FIG. 2A, the fluidized stent material 82 may be delivered into the void space 80 through the lumen 25 formed in the annular space between the outer sheath 24 and the inner shaft 26. The proximal end of the lumen 25 is connected by a port (not shown) to a source of fluidized stent material. In the embodiment shown in FIG. 2B, the fluidized stent material 82 may be delivered into the void space 80 through a plurality of ports 27 and a fluid lumen located in the inner shaft 26. The proximal end of the inner shaft lumen is connected by a port (also not shown) to a source of fluidized stent material. The stent material is introduced in a fluid state in order to fill the void space 80 created by the distal end 29 of the delivery catheter and the internal surface of the blood vessel 60.

As shown in FIG. 2C, in one embodiment, as the fluidized stent material 82 is delivered, it takes the shape of the void space 80, which is generally a cylindrical shape. Once the desired shape has been obtained, the fluid stent material 82 is allowed to harden, or caused to harden by a curing mechanism, as described more fully below.

FIG. 2D illustrates another embodiment, in which a molding balloon 74 is provided on the inner shaft 26. The molding balloon 74 is connected by an inflation lumen to an inflation source at the proximal end of the catheter. The molding balloon 74 is inflated after the fluid stent material 82 has been introduced into the void space 80. Inflating the molding balloon 74 causes the fluid stent material 82 to conform to the shape of the void space 80 at it is modified by the molding balloon 74. The molding balloon 74 may have a generally cylindrical profile, as illustrated in FIG. 2D, or it may have any other shape to achieve a desired shape for the molded stent, such as an hourglass shape, a tapered shape, a stepped shape, a barrel-shape, or others. The shape of the molding balloon 74 is imparted to the internal surface of the stent, as shown in FIG. 2D. The volume of stent material introduced and the inflation pressure of the molding balloon 74 may be selected so as to create a stent of desired size and shape within the vessel.

FIGS. 2E-F illustrate yet another embodiment, in which the molding balloon is formed integrally with the distal isolation balloon. In this embodiment, a single combination balloon 76 is used to both isolate the void space 80 and to shape or mold the fluid stent material 82 into a stent 84. The balloon 76 includes a distal portion 77 having a diameter suitable for sealing against the internal surface of the blood vessel, and a molding portion 78 having a diameter and shape suitable for molding and shaping the fluid stent material 82 against the internal wall 61 of the body lumen 60. The distal portion 77 of the balloon may be inflated initially with a secondary sheath 79 surrounding the molding portion 78 to isolate the void space 80 between the distal portion 77 and the proximal isolation balloon 70. Then, after the void space 80 has been filled with the liquid stent material 82, the molding portion 78 of the balloon may be expanded by retracting the secondary sheath 79 surrounding the molding portion 78 of the balloon 76 a sufficient distance to allow the molding portion 78 to expand in the void space 80. (See FIG. 2E). Once the secondary sheath 79 has been retracted such that its distal end is at the same position as the distal end of the outer sheath 24, the molding portion 78 of the balloon occupies a portion of the void space 80 extending from the distal portion 77 of the balloon to the proximal isolation balloon 70, thereby forming the stent material into a stent of suitable wall thickness and shape.

FIGS. 2G-I illustrate another embodiment of a distal portion of a stent delivery catheter in which a metal or polymer stent 86 is delivered to the treatment location prior to formation and delivery of a fluidized stent material at the same treatment location. As shown in FIG. 2G, the delivery catheter includes a proximal isolation balloon 70 fixed to the outer sheath 24 and a distal isolation balloon 72 fixed to the inner shaft 26. A nosecone 28 is fixed to the distal end of the inner shaft 26, and a guidewire 34 extends through a guidewire lumen located in the catheter.

The metal or polymer stent 86 is carried by the catheter in the annular lumen 25 between the outer sheath 24 and the inner shaft 26. When the outer sheath 24 is withdrawn, a selectable length of the metal or polymer stent 86 is exposed. The stent 86 may have any of a variety of common constructions, including helical structures, counterwound helical structures, expandable diamond structures, serpentine structures, or the like. Preferably, the stent 86 is formed in discrete segments and is delivered generally in a manner such as those taught in the aforementioned '813 and '713 applications, in order to provide the ability to deploy a stent 86 having a selectable length.

The stent 86 may be self-expanding, or it may be expanded by use of an expansion balloon 88 carried on the inner shaft 26. The expansion balloon 88 may be expanded, as shown in FIG. 2H, to expand the stent 86 sufficiently to engage the inner wall of the lumen, after which the balloon 88 is contracted, as shown in FIG. 2I. Once the balloon is contracted, a fluidized stent material 82 is injected through the annular lumen 25 into the void space to form a prosthesis. The fluidized stent material 82 is allowed or cause to cure or harden in the manner described elsewhere herein. The balloon 88 may be expanded during or after delivery of the fluidized stent material 82 in order to shape the fluidized material, similar to the manner described above in relation to FIG. 2D. Alternatively, the balloon 88 may not be used, and the prosthesis will be formed by the size of the inner shaft 26 to which is attached the uninflated balloon 88.

One or both of the stent 86 and the prosthesis formed from the fluidized material may be formed of biodegradable materials, such as those described previously herein. The materials making up the stent 86 and the prosthesis may biodegrade at the same or similar rates, or they may biodegrade at substantially different rates, depending upon the application and the desired treatment. In addition, one or both of the stent 86 and the prosthesis may carry a drug or other therapeutic material, either in a coating, or embedded or mixed in the material, or otherwise associated with the stent 86 or prosthesis.

FIGS. 3A-F illustrate another alternative embodiment of a distal portion 29 of the prosthesis forming and deploying apparatus. In this alternative embodiment, the fluid stent material 82 is delivered to the void space 80 by way of an inflatable balloon 176 having a plurality of holes 175, pores, or other ports, through which the fluid stent material passes. The proximal isolation balloon 70 is fixed to the outer sheath 24 near its distal end. An inflation lumen (not shown) is provided in the outer sheath 24 extending from the proximal isolation balloon 70 to the proximal end of the outer sheath 24 where it can be attached to a port and an inflation device to selectively expand or contract the proximal isolation balloon. A tapered nosecone 28 composed of a soft elastomeric material to reduce trauma to the vessel during advancement of the device, is fixed to the distal end 29 of the catheter 20.

Once the distal end 29 of the catheter is properly located at the site of a lesion 62 on the internal surface 61 of the blood vessel 60, the outer sheath 24 is retracted to expose an uninflated distal balloon 176 affixed to the distal end of the catheter. The uninflated distal balloon 176 typically has a length of about 20 mm to about 200 mm, more preferably about 40 mm to about 100 mm, extending proximally from near the distal end of the catheter and is generally covered by the outer sheath 24. When the outer sheath 24 is positioned over the distal balloon 176, it prevents the distal balloon from inflating. Only when the outer sheath 24 is retracted is the distal balloon 176 able to be expanded. Thus, the length of the expandable portion of the distal balloon 176 is able to be controlled by the amount that the outer sheath 24 is retracted.

Turning to FIG. 3B, the outer sheath 24 has been retracted a sufficient distance to enable the distal balloon 176, once inflated, to extend over the length of the lesion 62. The proximal isolation balloon 70 may then be expanded (see FIG. 3C) to seal off blood flow in the vessel. The distal balloon 176 is then inflated, preferably by injecting fluid stent material 82 into the balloon to cause the balloon to expand. The expanded distal balloon 176, as shown for example in FIG. 3D, preferably has a distal isolation portion 177 having a diameter suitable for engaging the inner surface of the vessel in order to seal off the void space 80 created in the blood vessel from distally of the lesion. The proximal portion 178 of the distal balloon has a relatively smaller diameter, thereby creating a void space 80 in the vessel between the inflated balloons and the vessel wall 61. The proximal portion 178 may be cylindrical or may have various other shapes to create a stent of desired shape.

A plurality of holes 175, pores, or another form of ports, are formed in the proximal portion 178 of the distal balloon, allowing the fluid stent material 82 to pass through the balloon into the void space 80. Thus, the action of inflating the balloon also causes the fluid stent material 82 to be delivered into the void space 80 created by the engagement of the balloons with the internal surface 61 of the blood vessel 60. Once the fluid stent material 82 has been delivered, it is allowed to harden or caused to harden to form a stent 84 at the lesion site within the blood vessel. See FIG. 3E. Once the stent 84 is formed and cured, the proximal isolation balloon 70 and distal balloon 176 are contracted, and the catheter 20 may be withdrawn. See FIG. 3F.

FIGS. 4A-D illustrate yet another alternative embodiment of a distal portion 29 of the prosthesis forming and deploying apparatus. In this alternative embodiment, the proximal isolation balloon 70 is fixed to the outer sheath 24 near its distal end. An inflation lumen (not shown) is provided in the outer sheath 24 extending from the proximal isolation balloon to the proximal end of the outer sheath 24 where it can be attached to a port and an inflation device to selectively expand or contract the proximal isolation balloon. A tapered nosecone 28 composed of a soft elastomeric material to reduce trauma to the vessel during advancement of the device, is fixed to the distal end 29 of the catheter 20.

Once the distal end of the catheter is properly located at the site of a lesion 62 on the internal surface 61 of the blood vessel 60, the outer sheath 24 is retracted to expose an uninflated distal balloon 76 extending from near the distal end of the catheter. The uninflated distal balloon 76 typically has a length of about 60 mm extending proximally from near the distal end of the catheter 20 and is generally covered by the outer sheath 24. When the outer sheath 24 is positioned over the distal balloon 76, it prevents the distal balloon 76 from inflating. Only when the outer sheath 24 is retracted is the distal balloon 76 able to be expanded. Thus, the length of the expandable portion of the distal balloon 76 is able to be controlled by the amount that the outer sheath 24 is retracted.

As shown in FIGS. 4A-B, the outer sheath 24 has been retracted a sufficient distance to enable the exposed portion of the distal balloon 76, once inflated, to extend over the length of the lesion 62. The proximal isolation balloon 70 may then be expanded (see FIGS. 4A-C) to seal off blood flow in the vessel 60. The distal balloon 76 is then inflated. The expanded distal balloon, as shown for example in FIG. 4A, preferably has a distal isolation portion 77 having a diameter configured to engage the inner wall of the vessel to seal off the void space 80 created in the blood vessel from distally of the lesion. The proximal portion 78 of the distal balloon has a relatively smaller diameter, thereby creating a void space 80 in the vessel between the inflated balloons and the vessel wall 61.

An annular stent material delivery passage 90 is provided between the outer sheath 24 and the distal balloon 76. Fluid stent material 82 may be injected into the void space 80 between the distal balloon 76 and the internal surface 61 of the blood vessel by way of the annular stent material delivery passage 90. See FIG. 4B. Once the fluid stent material 82 has been delivered, it is allowed to harden or caused to harden to form a stent 84 at the lesion site within the blood vessel. See FIG. 4C. Once the stent 84 is formed and cured, the proximal isolation balloon 70 and distal balloon 76 are contracted, and the catheter may be withdrawn. See FIG. 4D.

Figure 5C:
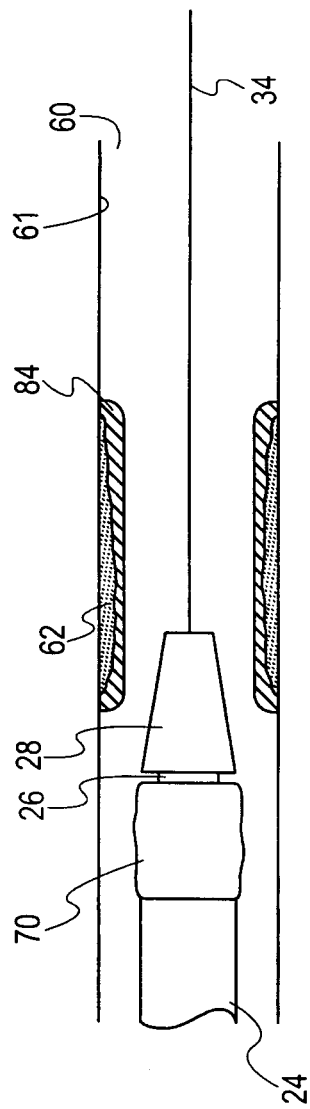
FIG. 5C is a side view, shown in partial cross-section, of the device shown in FIG. 5A, being withdrawn from the treatment location.

FIGS. 5A-C illustrate another alternative embodiment of a distal portion 29 of the prosthesis forming and deploying apparatus that employs a curing mechanism. In this alternative embodiment, the distal portion 29 of the catheter is generally similar to the structure described above in relation to FIGS. 4A-D, including a proximal balloon 70 attached to the outer sheath 24, a distal balloon 76 extending from near the distal end of the catheter beneath the outer sheath 24, and a tapered nosecone 28 attached to the distal end of the catheter. The distal balloon 76 is provided with a large diameter distal portion 77 for isolating the void space 80, and a smaller diameter molding portion 78 extending between the distal portion 77 and the proximal isolation balloon 70.

The distal balloon 76 is mounted to an internal shaft 26 near the distal end of the catheter. The internal shaft 26 is provided with a plurality of emitters 100 that are connected to an energy source (not shown) at the proximal end of the catheter 20. The energy source may be a source of ultraviolet, radio frequency, microwave, laser, or any other energy suitable for curing a liquid stent material 82. For example, the stent material may be of a type that more readily cures when exposed to a particular source of energy, or it may include an appropriate curing initiator that is susceptible to a particular source of energy, in which case the energy type and source is selected to be paired with the particular stent material being used. Several examples of materials, energy types, and combinations thereof are described, for example, in U.S. Pat. No. 6,039,757, which is incorporated herein by reference. Alternatively, the stent material may comprise, may include, or may be coated with a radiation-absorbing material that is expandable following exposure to radiation, as described in U.S. Pat. No. 6,607,553, which is incorporated herein by reference. The energy emitted will be capable of passing through the wall of the balloon 76 without damaging, deforming or weakening such wall material. Alternatively, the stent material may be infused or mixed with a curing material that facilitates curing of the stent material when exposed to the particular energy source. Several combinations of energy and material suitable for these purposes are possible, as will be readily understood by a person of skill in the art.

As shown in FIG. 5B, the emitters 100 emit the energy "E" radially outward from their locations on the internal shaft 26 to impinge on the fluid stent material 82. Preferably, the material used to form the distal balloon 76 is of a type that is permeable by the type of energy emitted from the emitters 100 on the internal shaft 26, such that the energy is transmitted through the distal balloon 76 into the stent material 82. After a sufficient amount of energy is emitted to cause the stent material 82 to cure (or to hasten curing), the energy emission is stopped. After the stent material 82 has hardened, the distal balloon 76 and proximal isolation balloon 70 may be contracted, and the catheter 20 removed from the treatment site (see FIG. 5C). It will be understood that emitters like those shown in FIGS. 5A-C may be used with any of the other embodiments described herein for curing the stent materials used in such embodiments.

For each of the embodiments described above in relation to FIGS. 2A-F, 3A-F, 4A-D, and 5A-C, the stent material is preferably any of several known materials suitable for use. Examples of suitable materials include several known polymers, metals, ceramics, proteins, or other materials that may be used in fluid form at room temperature and/or body temperature and that may be cured or hardened and remain sufficiently resilient while in contact with blood or other bodily fluids. Examples of polymers that may be used in the prostheses described herein are bioabsorbable or biocompatible polymers such as poly(lactide) (PLA), poly(glycolic acid) (PGA), poly(lactide-co-glycolide) (PLGA), and other polyhydroxyacids, polyethylene glycol (PEG), poly(caprolactone), polycarbonates, polyamides, polyanhydrides, polyamino acids, polyortho esters, polyacetals, degradable polycyanoacrylates and degradable polyurethanes. Various hardenable materials including 2-part epoxies, polyurethanes and other materials suitable for use with the invention are described in U.S. Pat. No. 6,875,212, which is incorporated herein by reference. Various other hardenable materials including compounds of proteins and polymers suitable for use with the invention are described in U.S. Pat. No. 6,371,975, which is incorporated herein by reference. Still other hardenable materials including compounds having an electrophilic polymer material and a nucleophilic polymer material in a buffer material suitable for use with the invention are described in U.S. Pat. No. 6,830,756, which is incorporated herein by reference. Examples of natural polymers and materials include proteins such as albumin, collagen, fibrin, fibrinogen, hydroxyapatite (HAp), and synthetic polyamino acids, and polysaccharides such as alginate, heparin, and other naturally occurring biodegradable polymers of sugar units. Additional suitable materials are also described in, for example, U.S. Pat. Nos. 5,059,211, 5,085,629, 5,147,385, 5,213,580, 5,670,161, 5,749,922, 5,947,977, 6,039,757, 6,607,553, and 6,623,519, each of which is incorporated herein by reference. Composites comprising any of the above materials combined with other biocompatible materials including metals, ceramics, carbon materials, and plastics may also be used to produce the desired strength, flexibility, elution, and bioerosion characteristics. Further, any of these materials may be used in combination with scaffolds, braids, or other strengthening materials, including woven metals or polymers, textile fabrics, metal or carbon fibers, and the like. In addition, these materials may be mixed not only with active therapeutic agents as described elsewhere herein, but with materials to enhance visibility via fluoroscopy, ultrasound, or magnetic resonance imaging. For example, fillers of radiopaque powders such as platinum, tantalum, tungsten, iridium, or gold may be combined with the materials above.

Each of the delivery catheter embodiments described above in relation to FIGS. 2A-F, 3A-F, 4A-D, and 5A-C, is capable of performing multiple in situ prosthesis formations and deliveries during a single interventional procedure, i.e., without fully withdrawing the catheter from the patient's vasculature. This is done by performing the procedures described above in relation to those Figures, then relocating the distal portion 29 of the delivery catheter to another treatment location, within the same vessel or another vessel, and performing the formation and delivery procedure again at the second treatment location. This may be repeated to form multiple prostheses of various lengths during a single procedure.

Figure 6A:
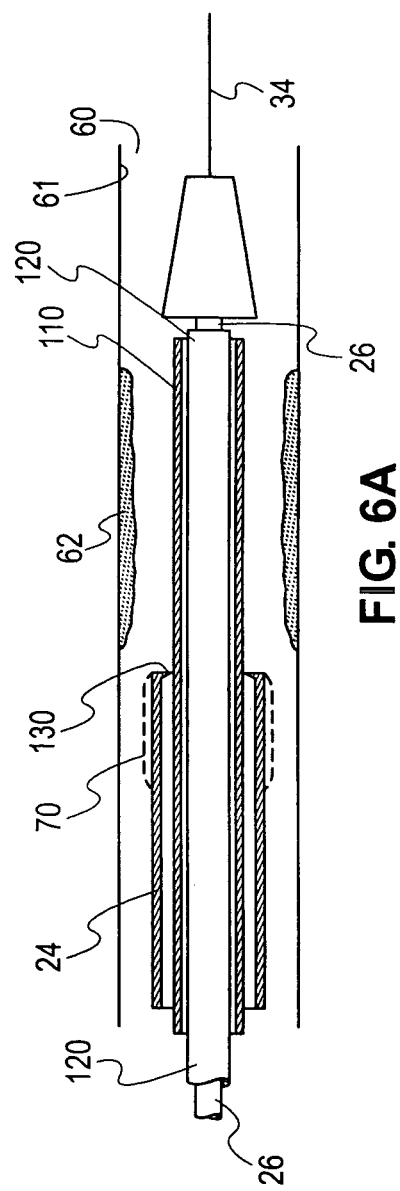
FIG. 6A is a side view, shown in partial cross-section, of another embodiment of a distal portion of a stent delivery catheter.

Turning to FIGS. 6A-C, the distal portion 29 of an alternative stent forming and deployment apparatus and method are described. This alternative apparatus and method include use of a formable tubular pre-stent member that is able to be formed at selected lengths and deployed at a treatment site, for example, within a blood vessel. The apparatus includes an outer sheath 24 disposed over a tubular pre-stent member 110 and an internal expandable member 120 (e.g., balloon). The expandable member 120 is attached to an internal shaft 26. A tapered nosecone 28 composed of a soft elastomeric material to reduce trauma to the vessel during advancement of the device, is fixed to the distal end 29 of the device 20. An optional proximal isolation balloon 70 may be included on the external surface of the outer sheath 24 near the distal end of the outer sheath.

The outer sheath 24 includes a cutting mechanism 130 at its distal end, preferably on the internal surface of the outer sheath 24. The cutting mechanism 130 may comprise a mechanical cutter such as a cutting blade, a heating element, an electrode, an electrolytic cutter, an ultrasonic cutter, a chemical cutter, or some other mechanism suitable for shearing, cutting, melting, or separating portions of the tubular pre-stent member 110. The cutting mechanism may be selectively actuated by a control member on the proximal handle 40, or may operate passively when contacted by the pre-stent member 110 during expansion. In the case of an electrode, electrolytic, ultrasonic, or heating element, the element or electrode is conductively connected to an energy source associated with the proximal handle 40 in a conventional manner.

The outer sheath 24 is preferably formed of a conventional catheter tubing having sufficient strength and flexibility to navigate the patient's vasculature, and also to restrict inflation of the portion of the expandable member 120 covered by the outer shaft 24. Examples of suitable materials include fiber reinforced polymers, particularly polyurethane. The expandable member 120 is preferably a conventional inflation balloon coupled by an inflation lumen to a source of inflation media associated with the proximal handle 40.

The tubular pre-stent member 110 may comprise any suitable material that is soft, flexible, and pliable in a first state for delivery and deployment, but subject to transformation into a rigid, relatively stronger second state to perform a scaffolding function at a treatment site in, for example, a blood vessel 60. Suitable materials include those described above in relation to the fluid stent materials used in the devices illustrated in FIGS. 2A-F, 3A-F, 4A-D, and 5A-C. The transformation is preferably made by curing or hardening the pre-stent member 110 into a final deployed stent as described above in connection with other embodiments.

Turning to FIG. 6A, the catheter 20 is delivered to a location within the blood vessel 60 having a lesion 62 or other defect requiring treatment. The distal portion 29 of the catheter is advanced sufficiently that the distal tip 28 is distal of the treatment site. The outer sheath 24 is then retracted to expose the pre-stent member 110. The longitudinal distance that the outer sheath 24 is retracted determines the length of the pre-stent member 110 that ultimately will be deployed, thus allowing the operator to select the length of the stent to match the length of the lesion being treated.

Once the outer sheath 24 is retracted, the proximal isolation balloon 70, if present, may be expanded to isolate the treatment site from blood flow. (See FIG. 6B). The expandable member 120 is then expanded, causing the pre-stent member 110 to expand with the expandable member 120 and to conform with the internal surface 61 of the blood vessel at the treatment site. The expandable member 120 is only allowed to expand in the region that has been uncovered by the outer sheath 24, thereby expanding the pre-stent member 110 over the length of the treatment location. The pre-stent member 110 is then cut using the cutting mechanism 130, thereby creating a free tubular pre-stent member 110 fully expanded at the treatment location.

Once the pre-stent member 110 is expanded and cut, the expandable member 120 is maintained in its expanded state a sufficient amount of time to allow the pre-stent member 110 to cure or harden. (See FIG. 6C). Curing or hardening may result from passage of a sufficient amount of time to allow the material to harden by itself, or curing may be facilitated by a curing mechanism. For example, the pre-stent member material may be of a type that is caused to transform into a rigid, resilient material due to the stress incurred during the balloon expansion step. The pre-stent member may also further harden after sufficient time has passed after the expansion step. Curing may be further facilitated by exposure to a heating or cooling medium delivered into the expandable member 120. Alternatively, an energy source may be used to transmit ultraviolet, radio frequency, microwave, laser, or other energy to the flexible pre-stent member to cause it to cure after deployment. For example, one of the curing mechanisms described above in relation to FIGS. 5A-C may be utilized to cure the pre-stent member 110 after deployment. In either case, the pre-stent member 110 is allowed or caused to cure such that the resulting stent 84 has sufficient radial strength and resilience to perform the desired stent scaffolding function.

After the pre-stent member 110 has been allowed or caused to harden, the expandable member 120 may be contracted and retracted inside the outer sheath 24. The catheter 20 may then be relocated to another treatment site within the target vessel or another vessel and the procedure repeated for deployment of another stent, or the catheter may be completely withdrawn.

Figure 7A:
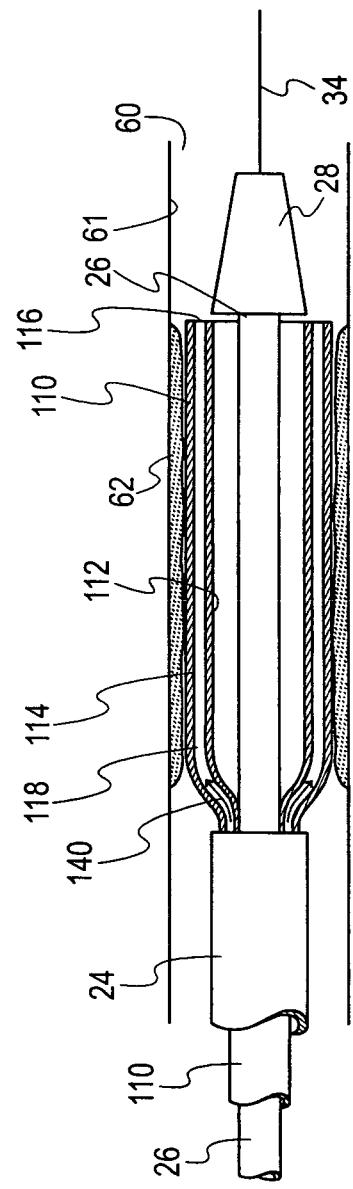
FIG. 7A is a side view, shown in partial cross-section, of another embodiment of a distal portion of a stent delivery catheter.
Figure 7B:
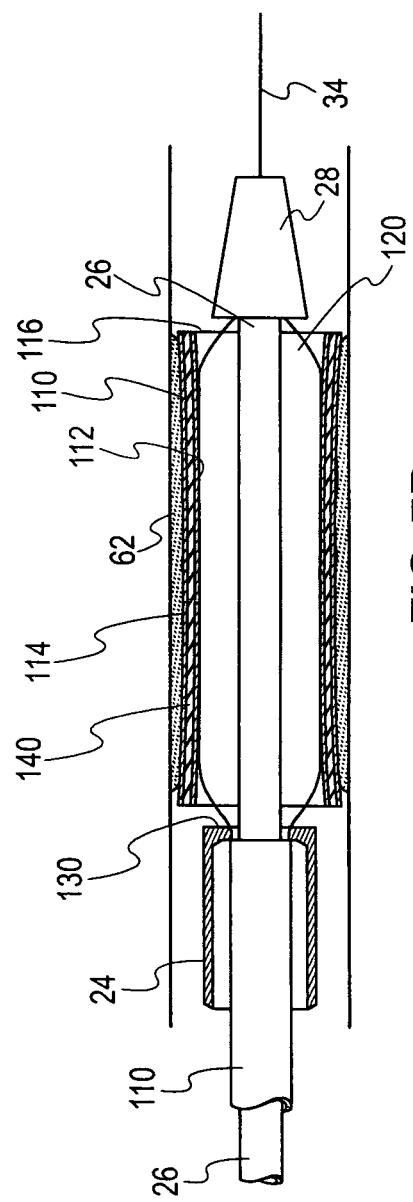
FIG. 7B is a side view, shown in partial cross-section, of the device shown in FIG. 7A, after shearing of a pre-stent member.
Figure 8D:
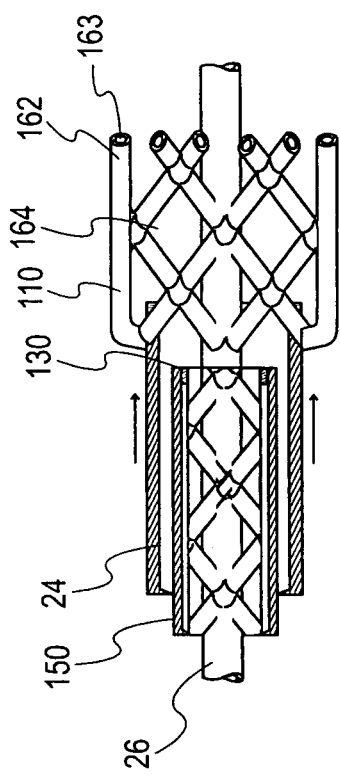
FIG. 8D is a side view, shown in partial cross-section, of the device shown in FIG. 8A, further illustrating shearing of a pre-stent member.
Figure 8C:
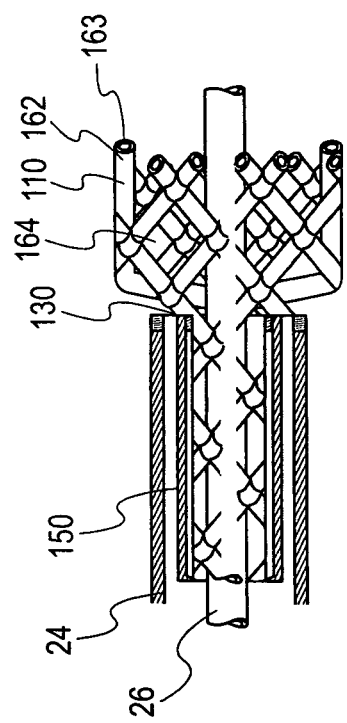
FIG. 8C is a side view, shown in partial cross-section, of the device shown in FIG. 8A, illustrating shearing of a pre-stent member.
Figure 8E:
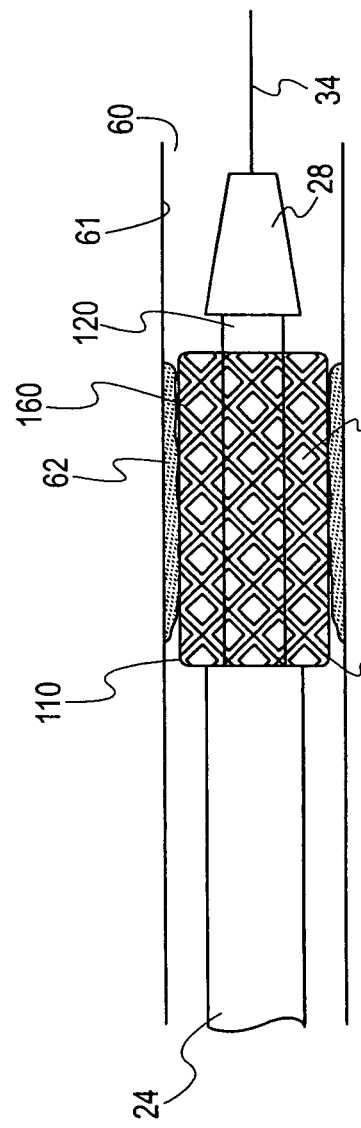
FIG. 8E is a side view of the device shown in FIG. 8A, after shearing of a pre-stent member.

Turning to FIGS. 7A-B, the distal portion 29 of another alternative stent forming and deployment apparatus and its method of use are illustrated. This alternative apparatus and method include use of an inflatable tubular pre-stent member 110 that is able to be formed at selected lengths and deployed at a treatment site, for example, within a blood vessel. The apparatus includes an outer sheath 24 disposed over an inflatable tubular pre-stent member 110. An optional internal expandable member 120 (e.g., a balloon) may also be included in some embodiments. When it is present, the expandable member 120 is attached to an internal shaft 26. A tapered nosecone 28 composed of a soft elastomeric material to reduce trauma to the vessel during advancement of the device, is fixed to the distal end 29 of the device 20. An optional proximal isolation balloon (not shown) may be included on the external surface of the outer sheath 24 near the distal end of the outer sheath.

The outer sheath 24 includes a cutting mechanism 130 at its distal end, preferably on the internal surface of the outer sheath. The cutting mechanism 130 may comprise a mechanical cutter such as a cutting blade, a heating element, an electrode, an electrolytic cutter, an ultrasonic cutter, a chemical cutter, or some other mechanism suitable for shearing or separating portions of the tubular pre-stent member 110. The cutting mechanism may be actuated by a control member on the proximal handle 40, or may operate passively when contacted by the pre-stent member 110 upon expansion thereof. In the case of an electrode, electrolytic, ultrasonic, or heating element, the element or electrode is conductively connected to an energy source associated with the proximal handle 40 in a conventional manner.

The outer sheath 24 is preferably formed of a conventional catheter tubing having sufficient strength and flexibility to navigate the patient's vasculature, and also to restrict inflation of the portion of the expandable member 120 covered by the outer sheath 24. Examples of suitable materials include fiber reinforced polymers, particularly polyurethane. The expandable member 120, when present, is preferably a conventional inflation balloon coupled by an inflation lumen to a source of inflation media associated with the proximal handle 40.

The tubular pre-stent member 110 is a generally tubular structure having an internal wall 112, an external wall 114, an end wall 116, and an annular lumen 118 between the internal and external walls. The lumen 118 is in fluid communication with a fluid delivery lumen in the shaft of the device which connects to a source of filling material 140 associated with the proximal handle 40. In some embodiments, the walls of the pre-stent member 110 are formed of a material having resilience sufficient to cause the pre-stent member to expand radially outward when the outer sheath 24 is retracted. Preferably, the internal, external, and end walls of the pre-stent member are formed of a polymer material, a metal or metal alloy, or a blend of two or more of these materials. Examples of suitable materials include those fluid stent materials described above in relation to the delivery catheters illustrated in FIGS. 2A-F, 3A-F, 4A-D, and 5A-C.

Turning to FIG. 7A, the catheter 20 is delivered to a location within the blood vessel 60 having a lesion 62 or other defect requiring treatment. The distal portion 29 of the catheter is advanced sufficiently that the distal tip 28 is distal of the treatment site. The outer sheath 24 is then retracted to expose the inflatable pre-stent member 110. The longitudinal distance that the outer sheath 24 is retracted determines the length of the pre-stent member 110 that ultimately will be deployed.

Once the outer sheath 24 is retracted, a fluid or filler material 140 is delivered to the annular lumen 118 formed in the pre-stent member 110, thereby filling the annular lumen 118. The fluid or filler material 140 may be any suitable material that provides desired physical properties to the stent. Preferably, the fluid or filler material 140 is a polymer or foam that is subject to hardening or curing once delivered into the annular lumen 118.

In one embodiment, injection of the fluid or filler material 140 causes the pre-stent member 110 to expand to conform with the internal wall 61 of the blood vessel 60 at the treatment location. In alternative embodiments, the pre-stent member 110 may partially or fully self-expand to conform with the internal wall of the blood vessel prior to injecting the fluid or filler material 140. In those embodiments in which the pre-stent member 110 is not self-expanding, or when additional expansion is desired, the pre-stent member 110 may be expanded or further expanded by an expandable member 120 provided on the internal shaft 26.

After the fluid or filler material 140 is delivered to the annular lumen 118, the pre-stent member 110 is cut using the cutting mechanism 130 on the outer sheath 24, thereby creating a free tubular pre-stent member 110 fully expanded within the blood vessel 60. The cutting step may be performed after the fluid or filler material 140 has hardened or cured sufficiently to prevent leakage from the cut portion of the pre-stent member 110. Alternatively, the cutting member 130 may optionally seal the pre-stent member, such as by cauterization (melting the stent material) or mechanically sealing, to prevent the fluid or filler material from leaking from the proximal end of the pre-stent member 110.

Once the pre-stent member 110 is expanded and cut, if the expandable member 120 has been used, the expandable member 120 is maintained in its expanded state a sufficient amount of time to allow the pre-stent member 110 to cure or harden. (See FIG. 7B). Curing or hardening may result from passage of a sufficient amount of time to allow the fluid or filler material 140 and the pre-stent member walls to harden by itself, or curing may be facilitated by a curing mechanism. For example, the pre-stent member material may be of a type that is caused to transform into a rigid, resilient material due to the stress incurred during the balloon expansion step. In such a case, the pre-stent member 110 will harden after sufficient time has passed after the expansion step. Curing may be further facilitated by exposure to a heating or cooling medium delivered into the expanded balloon. Alternatively, an energy source may be used to transmit ultraviolet, radio frequency, microwave, laser, or other energy to the flexible pre-stent member to cause it to cure after deployment. For example, one of the curing mechanisms described above in relation to FIGS. 5A-C may be utilized to cure the pre-stent member 110 after deployment. In either case, the pre-stent member 110 is allowed or caused to cure such that the resulting stent 84 has sufficient radial strength and resilience to perform the desired stent scaffolding function.

After the pre-stent member has been allowed or caused to harden, the expandable member 120 may be contracted and retracted inside the outer sheath 24. The catheter 20 may then be relocated to another treatment location and the procedure repeated for deployment of another stent, or the catheter may be completely withdrawn.

FIGS. 8A-E illustrate the distal portion of another alternative stent forming and deployment apparatus and method. This alternative apparatus and method include use of another form of inflatable tubular pre-stent member that is able to be formed at selected lengths and deployed at a treatment site, for example, within a blood vessel. The apparatus includes an outer sheath 24 and a middle shaft 150 disposed over an inflatable tubular pre-stent member 110. An optional internal expandable member 120 (e.g., a balloon) may also be included in some embodiments. When it is present, the expandable member 120 is attached to an internal shaft 26. A tapered nosecone 28 composed of a soft elastomeric material to reduce trauma to the vessel during advancement of the device, is fixed to the distal end 29 of the device 20. An optional proximal isolation balloon (not shown) may be included on the external surface of the outer sheath 24 near the distal end of the outer sheath.

In the embodiment shown in FIGS. 8A-E, a cutting mechanism 130 is located at the distal end of the middle shaft 150. (See FIGS. 8C-D). The cutting mechanism 130 may comprise a mechanical cutter such as a cutting blade, a heating element, an electrode, an electrolytic cutter, an ultrasonic cutter, a chemical cutter, or some other mechanism suitable for shearing or separating portions of the tubular pre-stent member 110. The cutting mechanism may be actuated by a control member on the proximal handle 40, or may operate passively as in other embodiments. In the case of an electrode, electrolytic, ultrasonic, or heating element, the element or electrode is conductively connected to an energy source associated with the proximal handle 40 in a conventional manner.

The outer sheath 24 and middle shaft 150 are preferably formed of conventional catheter tubing having sufficient strength and flexibility to navigate the patient's vasculature, and also to restrict inflation of the expandable member. Examples of suitable materials include fiber reinforced polymers, particularly polyurethane. The expandable member 120, when present, is preferably a conventional inflation balloon coupled by an inflation lumen to a source of inflation media associated with the proximal handle 40.

The tubular pre-stent member 110 is a generally tubular structure comprising a lattice 160 of interconnected tubes 162 each having lumens 163 therein. In the embodiment shown in FIGS. 8A-E, the lattice 160 is in the form of a plurality of diamond shapes in which the interconnected tubes 162 form a geometric matrix defining empty or void spaces 164 having a diamond shape. Other variations of this lattice shape are possible, such as lattices defining circular, triangular, square, pentagonal, wave-shaped, zig-zag, and other repeating patterns, or combinations of such patterns. Still further variations may include irregular void spaces. Each of these variations, or combinations thereof, may be employed, as will be readily understood by persons of skill in the art. The interconnected tubes 162 are, in turn, in fluid communication with a source of fluid filling material associated with the proximal handle 40. In some embodiments, the interconnected tubes 162 of the pre-stent member 110 are formed of a material having resilience sufficient to cause the pre-stent member to expand radially outward when the outer sheath 24 is retracted. Preferably, the tubes 162 of the pre-stent member are formed of a polymer material, a metal or metal alloy, or a blend of two or more of these materials. Examples of suitable materials include the fluid stent materials described above in relation to the delivery catheters illustrated in FIGS. 2A-F, 3A-F, 4A-D, and 5A-C.

Turning to FIG. 8A, the catheter 20 is delivered to a location within the blood vessel 60 having a lesion or other defect requiring treatment. The distal portion 29 of the catheter is advanced sufficiently that the distal tip is distal of the treatment site. The outer sheath 24 is then retracted to expose the inflatable pre-stent member 110. The longitudinal distance that the outer sheath 24 is retracted determines the length of the pre-stent member 110 that ultimately will be deployed.

Once the outer sheath 24 is retracted, a fluid or filler material 140 is delivered to the lumens 163 formed in the body of the pre-stent member, thereby filling the lumens 163. The fluid or filler material 140 may be any suitable material that provides desired physical properties to the stent. Preferably, the fluid or filler material 140 is a polymer or foam that is subject to hardening or curing once delivered into the annular lumen.

In one embodiment, injection of the fluid or filler material causes the pre-stent member 110 to expand to conform with the internal wall 61 of the blood vessel 60 at the treatment location. In alternative embodiments, the pre-stent member 110 may partially or fully self-expand to conform with the internal wall 61 of the blood vessel 60 prior to injecting the fluid or filler material 140. In those embodiments in which the pre-stent member 110 is not self-expanding, or when additional expansion is desired, the pre-stent member may be expanded or further expanded by an expandable member 120 provided on the internal shaft 26.

After the fluid or filler material 140 is delivered to the pre-stent lumens 163, the pre-stent member 110 is cut using the cutting mechanism 130 on the middle shaft 150, thereby creating a free tubular pre-stent member 110 fully expanded within the blood vessel 60. The cutting step may be performed by advancing the middle shaft 150 relative to the outer sheath 24 and the pre-stent member 110, thereby causing the cutting mechanism 130 to engage and cut the pre-stent member 110 at the contact point with the cutting mechanism 130. The cutting step may be performed after the fluid or filler material 140 has hardened or cured sufficiently to prevent leakage from the cut portion of the pre-stent member. Alternatively, the cutting member 130 may optionally seal the pre-stent member 110, such as by cauterization (melting the stent material) or mechanically sealing, to prevent the fluid or filler material from leaking from the proximal end of the pre-stent member 110.

Once the pre-stent member 110 is expanded and sheared, if the expandable member 120 has been used, the expandable member 120 is maintained in its expanded state a sufficient amount of time to allow the pre-stent member 110 to cure or harden. (See FIG. 8E). Curing or hardening may result from passage of a sufficient amount of time to allow the fluid or filler material 140 and the pre-stent member tubes 162 to harden by itself, or curing may be facilitated by a curing mechanism. For example, the pre-stent member material may be of a type that is caused to transform into a rigid, resilient material due to the stress incurred during the balloon expansion step. The pre-stent member may also harden after sufficient time has passed after the expansion step. Curing may be further facilitated by exposure to a heating or cooling medium delivered into the expanded balloon or other vessel. Alternatively, an energy source may be used to transmit ultraviolet, radio frequency, microwave, laser, or other energy to the pre-stent member to cause it to cure after deployment. For example, one of the curing mechanisms described above in relation to FIGS. 5A-C may be utilized to cure the pre-stent member after deployment. In either case, the pre-stent member 110 is allowed or caused to cure such that the resulting stent has sufficient radial strength and resilience to perform the desired stent scaffolding function.

After the pre-stent member 110 has been allowed or caused to harden, the expandable member 120 (where used) may be contracted and retracted inside the outer sheath 24. The catheter 20 may then be relocated to another treatment site and the procedure repeated for deployment of another stent 84, or the catheter 20 may be completely withdrawn.

Figure 9B:
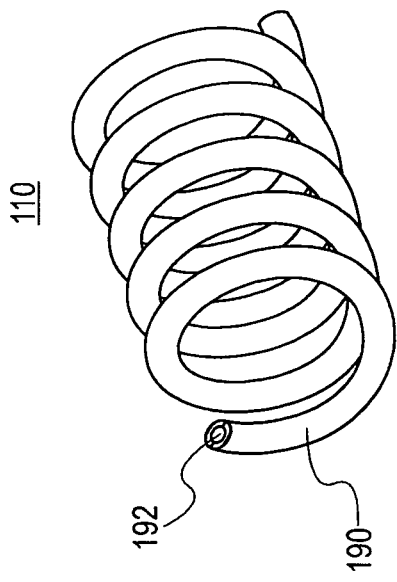
FIG. 9B illustrates a portion of a coil-shaped pre-stent member.
Figure 9C:
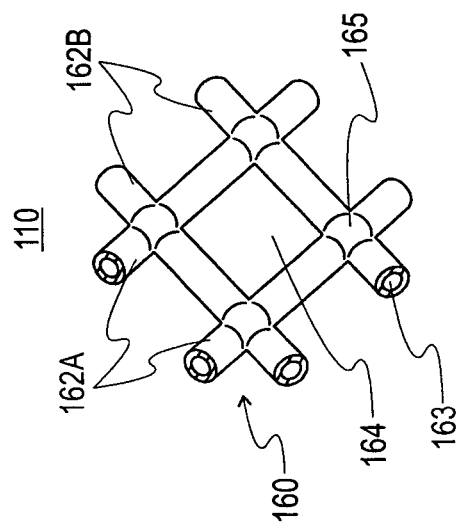
FIG. 9C illustrates a portion of a lattice-shaped pre-stent member.
Figure 9A:
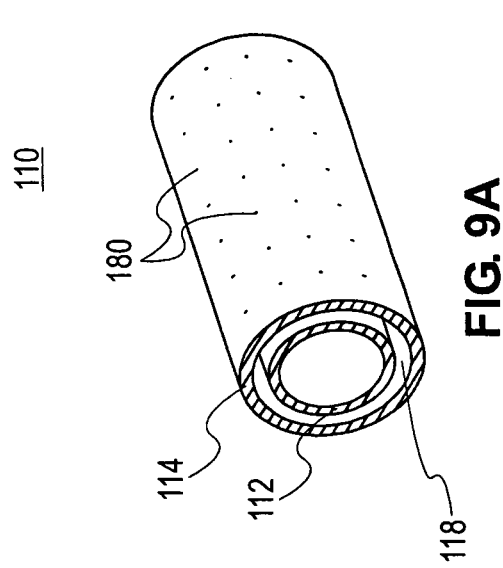
FIG. 9A illustrates a portion of a cylindrical pre-stent member.

FIGS. 9A-C illustrate alternative embodiments of inflatable pre-stent members 110 suitable for use in the apparatus and methods described above in relation to FIGS. 7A-B and 8A-E. The first embodiment, shown in FIG. 9A, comprises a generally cylindrical member having a cylindrical internal wall 112 and a cylindrical external wall 114, with the internal wall having a smaller diameter than the external wall. A fluid filler lumen 118 is provided between the internal and external walls to receive a fluid or filler material during deployment of the pre-stent member. A plurality of ports 180, such as pinholes, are provided on the external surface of the external wall 114 of the pre-stent member 110. The ports are provided to facilitate transmission of therapeutic materials, such as drugs, that may be provided in the filler or fluid 140.

FIG. 9B illustrates a coil-shaped pre-stent member 110 comprising a single tube 190 formed in the shape of a coil. The tube 190 is provided with a fluid lumen 192 for injecting the fluid or filler material 140 during deployment of the pre-stent member. The coil may be partially or fully radially self-expanding, radial expansion may be partially or fully obtained by injecting the fluid or filler material 140 through the lumen 192, or the coil may be partially or fully expanded using an expandable member 120, such as a balloon. Although not shown, the coil-shaped pre-stent member may also be provided with ports, such as pinholes, to facilitate transmission of therapeutic materials contained in the filler or fluid.

FIG. 9C illustrates a portion of a tubular lattice 160 that may be used to form a pre-stent member 110. The tubular lattice 160 shown in FIG. 9C includes a first pair of parallel tubes 162a that intersect a second pair of parallel tubes 162b, the first and second pair of tubes being perpendicular to each other. The lattice 160 defines a diamond-shaped void space 164 between the pairs of tubes. As described above, other geometric patterns are also possible using the tubular-shaped members shown in this embodiment. Each of the tubes 162 includes a fluid lumen 163 suitable for injecting a fluid or filler. The fluid lumens 163 of each tube intersect the fluid lumens 163 of perpendicular tubes at intersections 165 that are also open to fluid communication. As with the embodiments illustrated in FIGS. 9A-B, the tubes 162 forming the tubular lattice 160 may also be provided with ports 180, such as pinholes, to facilitate transmission of therapeutic materials contained in the filler or fluid.

A tubular lattice such as that illustrated in FIG. 9C and other cylindrical patterns of tubular elements may be formed in various ways. In one exemplary method, a polymeric double-walled cylindrical tube like that shown in FIG. 9A is placed on a rotatable mandrel. A laser, preferably mounted on a servo-controlled X-Y positioner, is then used to melt or heat bond selected regions of the double-walled tube in a desired pattern to create an interconnected lattice of hollow elements or struts. The regions of the tube between the hollow elements may then be cut or melted away by the laser. For example, the laser could be directed to form a plurality of diamond-shaped patterns where the inner and outer walls of the tube are melted together. The regions of the tube within each diamond are then cut out, leaving a criss-cross pattern of interconnected hollow struts similar to that shown in FIG. 9C. Of course, prior to introduction of liquid stent material, each strut would not have a cylindrical cross-section as shown, but would instead have flat inner and outer walls joined together at their edges.

Figure 10C:
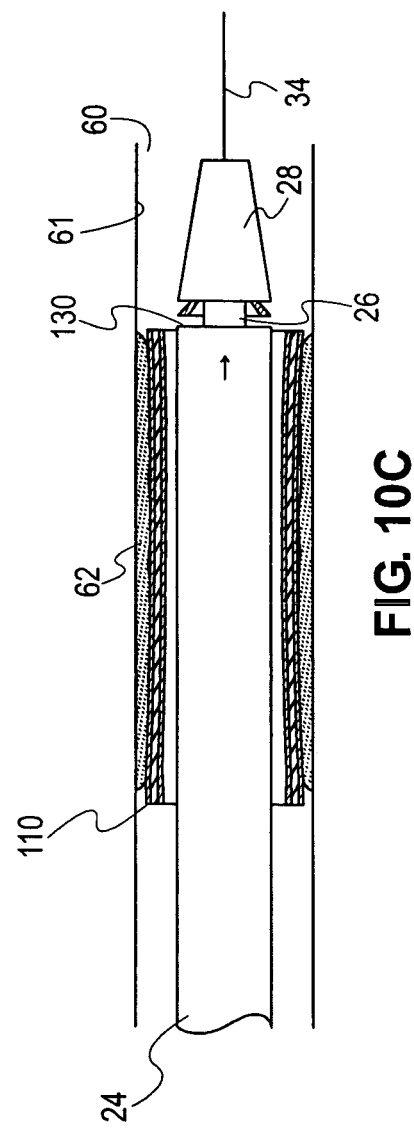
FIG. 10C is a side view, shown in partial cross-section, of the device shown in FIG. 10A, illustrating shearing of the distal end of the pre-stent member.

Turning to FIGS. 10A-C, the distal portion of another alternative stent forming and deployment apparatus and its method of use are illustrated. This alternative apparatus and method include use of another form of an inflatable tubular pre-stent member 110 that is able to be formed at selected lengths and deployed at a treatment site, for example, within a blood vessel. The apparatus includes an outer sheath 24 disposed over an inflatable tubular pre-stent member 110. An internal shaft 26 is provided. An optional middle shaft 150 may also be provided beneath the outer sheath 24 and above the inflatable pre-stent member 110. A tapered nosecone 28 composed of a soft elastomeric material to reduce trauma to the vessel during advancement of the device, is fixed to the distal end 29 of the device 20. An optional proximal isolation balloon 70 (not shown) may be included on the external surface of the outer sheath near the distal end of the outer sheath.

The outer sheath 24 includes a cutting mechanism 130 at its distal end, preferably on the internal or distal end surface of the outer sheath 24. The cutting mechanism 130 may comprise a mechanical cutter such as a cutting blade, a heating element, an electrode, an electrolytic cutter, an ultrasonic cutter, a chemical cutter, or some other mechanism suitable for shearing, cutting, melting, or separating portions of the tubular pre-stent member 110. The cutting mechanism may be actuated by a control member on the proximal handle 40, or it may operate passively when contacted by the pre-stent member 110 during expansion. In the case of an electrode, electrolytic, ultrasonic, or heating element, the element or electrode is conductively connected to an energy source associated with the proximal handle 40 in a conventional manner.

The outer sheath 24 and optional middle shaft 150 are preferably formed of conventional catheter tubing having sufficient strength and flexibility to navigate the patient's vasculature, and also to restrict inflation of the portion of the inflatable pre-stent member 110 covered by the outer and/or middle sheath. Examples of suitable materials include fiber reinforced polymers, particularly polyurethane.

The tubular pre-stent member 110 is a generally tubular structure that is relatively soft and pliable. The distal end of the pre-stent member 110 is attached to the internal shaft 26 at a point near the proximal end of the nosecone 28, and the pre-stent member 110 extends proximally from that point beneath the outer sheath 24. Preferably, the pre-stent member 110 is formed of a polymer material, a metal or metal alloy, or a blend of two or more of these materials. Examples of suitable materials include the fluid stent materials described above in relation to the delivery catheters illustrated in FIGS. 2A-F, 3A-F, 4A-D, and 5A-C.

The internal shaft 26 extends beneath the pre-stent member 110 proximally from near the distal end of the catheter. The internal shaft 26 is provided with a plurality of emitters 110 that are connected to an energy source (not shown) at the proximal end of the catheter. The energy source may be a source of ultraviolet, radio frequency, microwave, laser, or any other energy suitable for curing a material used to form the pre-stent member 110. For example, the pre-stent member material may be of a type that more readily cures when exposed to a particular source of energy, or it may include an appropriate curing initiator that is susceptible to a particular source of energy, in which case the energy type and source is selected to be paired with the particular stent material being used. Several examples of materials, energy types, and combinations thereof are described, for example, in U.S. Pat. No. 6,039,757, which is incorporated herein by reference. Alternatively, the stent material may comprise, may include, or may be coated with a radiation-absorbing material that is expandable following exposure to radiation, as described in U.S. Pat. No. 6,607,553, which is incorporated herein by reference. Alternatively, the pre-stent member material may be infused or coated with a curing material, such as an ultraviolet curable polymer, that facilitates curing of the stent material when exposed to the particular energy source. Several combinations of energy and material suitable for these purposes are possible, as will be readily understood by a person of skill in the art.

Turning to FIG. 10A, the catheter 20 is delivered to a location within the blood vessel 60 having a lesion 62 or other defect requiring treatment. The distal portion 29 of the catheter is advanced sufficiently that the distal tip 28 is distal of the treatment site. The outer sheath 24 is then retracted to expose the inflatable pre-stent member 110. The longitudinal distance that the outer sheath 24 is retracted determines the length of the pre-stent member 110 that ultimately will be deployed.

Once the outer sheath 24 is retracted, the pre-stent member 110 is inflated by injecting an inflation medium into the pre-stent member 110 by way of either an annular lumen 200 between the pre-stent member 110 and the internal shaft, or by an inflation lumen located in the internal shaft 26. In either case, the inflation lumen is in fluid communication with a source of inflation medium at the proximal handle 40. Inflation of the pre-stent member 110 causes the pre-stent member to expand between the distal point that the pre-stent member is attached to the internal shaft 26, and the proximal point at which inflation is restricted by the outer sheath 24 (or middle sheath 150, where present). Expansion of the pre-stent member 110 causes the pre-stent member to conform to the internal surface 61 of the blood vessel 60 at the treatment location.

As shown in FIG. 10A, after the pre-stent member 110 has been expanded, the emitters 100 emit energy "E" radially outward from their locations on the internal shaft 26 to impinge on the pre-stent member 110. After a sufficient amount of energy is emitted to cause the pre-stent material to cure (or to hasten curing), the energy emission is stopped.

After curing, the fluid used to inflate the pre-stent member 110 is withdrawn by suction on the fluid delivery lumen in the catheter. The pre-stent member 110 is then cut using the cutting mechanism 130 on the outer sheath 24. The outer sheath 24 is advance distally until it encounters and cuts the proximal end of the pre-stent member 110. (See FIG. 10B). The outer sheath 24 is then advanced further distally, internally of the pre-stent member 110, until the outer sheath 24 encounters and cuts the distal end of the pre-stent member 110, detaching it from the internal shaft 26. (See FIG. 10C). After cutting, the catheter 20 may be withdrawn.

The prostheses described herein in each of the above embodiments may also be combined or used in conjunction with other stent structures. For example, the prostheses described herein may be formed and delivered to a treatment location already having a metallic stent, or simultaneously with another metallic or other stent, in order to provide additional scaffolding, to deliver therapeutic materials contained on or in the prosthesis, or other functions. In several embodiments, a biodegradable material may be used to form a prosthesis that is used in conjunction with a pre-existing metallic or other more permanent stent, such that the metallic or more permanent stent remains in place after the biodegradable prosthesis has been absorbed or otherwise degraded.

In addition, in each of the embodiments described herein, the prosthesis material may be combined with a drug or other therapeutic agent that inhibits restenosis, reduces thrombus formation or has other therapeutic effects. The drug or agent may be mixed with the prosthesis material and introduced with it to form the prosthesis, or the drug may be introduced into the isolated region separately from the prosthesis material, either simultaneously, before, or after introduction of the prosthesis material. For example, the prosthesis material and drug could be introduced in an alternating fashion so that the prosthesis has a sandwich structure with separate layers of drug and prosthesis material. Examples of drugs that may be included in the foregoing structures include taxol, rapamycin, analogs of rapamycin such as Everolimus, Biolimus A9, or ABT 578, thrombolytics such as heparin, as well as VEGF, gene therapy agents, and a range of other agents known to those of ordinary skill in the art.

The preferred embodiments of the invention are described above in detail for the purpose of setting forth a complete disclosure and for the sake of explanation and clarity. Those skilled in the art will envision other modifications within the scope and spirit of the present disclosure. Such alternatives, additions, modifications, and improvements may be made without departing from the scope of the present invention, which is defined by the claims.

What is claimed is:

1. An apparatus for delivering a prosthesis into a target vessel having a vessel wall with a vessel diameter comprising:
   a flexible catheter body having proximal and distal portions, said flexible catheter body having a first expandable member carried at or near the distal portion thereof and a second expandable member carried at an adjustable distance proximal to the first expandable member, at least a portion of the first and second expandable members being expandable to the vessel diameter to engage the vessel wall, the distance between the first and second expandable members being adjustable,
   a therapeutic material comprising a fluidized stent material which is in fluid communication with an exterior of the apparatus through a passageway in the catheter body;
   a molding member positioned along the catheter body and integrally formed with the first expandable member such that the molding member and first expandable member form a single inflatable balloon in fluid communication with one another and the molding member is expandable in a proximal direction from the first expandable member and has an expanded length which is adjustable to correspond to the distance between the first and second expandable members, the molding member further having an expanded profile which, during use of the apparatus, conforms the therapeutic material against the vessel wall in a selected shape and where the expanded profile is shaped to be different from an expanded profile of the first and second expandable members; and,
   a secondary sheath which is adjustably positionable over the molding member and is further longitudinally positionable independent of a location of the first and second expandable members, where a position of the secondary sheath controls expansion of the molding member independently from the first and second expandable members,
   wherein said first expandable member and said second expandable member, when inflated to the vessel diameter, define a void space around the distal portion of the catheter body which is unoccupied by any portion of the apparatus prior to delivery of the prosthesis, the void space being in fluid communication with the therapeutic material and having a length dimension between a proximal surface of the first expandable member and a distal surface of the second expandable member that is adjustable by adjusting the positions of the proximal surface of the first expandable member relative to the distal surface of the second expandable member.

2. The apparatus of claim 1, wherein the first expandable member is mounted to an inner shaft, and the second expandable member is mounted to an outer sheath axially slidable relative to the inner shaft, no part of the second expandable member being mounted to the inner shaft.

3. The apparatus of claim 2, wherein the passageway comprises a lumen in fluid communication with the void space.

4. The apparatus of claim 1, wherein the molding member is expandable to an expanded diameter less than the vessel diameter, where the void space surrounds the molding member.

5. The apparatus of claim 1, wherein said first expandable member has a first diameter and said molding member has a second diameter, said first diameter being larger than said second diameter.

6. The apparatus of claim 5, wherein said first expandable member is located distally from said molding member.

7. The apparatus of claim 1, wherein, during use of the apparatus, the length dimension of the void space is adjusted by the operator of the apparatus at least in part by adjusting a position of at least one of the first or second expandable members relative to another of the first or second expandable members which remains stationary relative to the vessel wall.

8. The apparatus of claim 1, wherein the length dimension of the void space may be adjusted by the operator of the apparatus.

9. The apparatus of claim 1, wherein the therapeutic material is configured to be cured or hardened while remaining resilient.

10. A method of forming a prosthesis in a target vessel of a patient comprising:
    introducing a distal portion of a catheter into the target vessel;
    positioning a first portion of the catheter at a target location in the target vessel;
    axially moving a proximal isolation member carried on the catheter relative to a distal isolation member carried on the catheter to create an adjusted distance therebetween;
    expanding the distal isolation member;
    expanding the proximal isolation member so as to create a void space surrounding the distal portion of the catheter between a proximal surface of the distal isolation member and a distal surface of the proximal isolation member such that the void space is adjustable by adjusting a position of the surfaces relative to one another and is isolated from the remainder of the target vessel, the void space being unoccupied by any portion of the catheter;
    introducing a liquid prosthetic material into the void space;
    adjusting a longitudinal position of a secondary sheath positioned over a molding member, where the longitudinal position of the secondary sheath is adjusted independently from the distal and proximal isolation members;
    expanding the molding member in a proximal direction from the distal isolation member between the distal and proximal isolation members where the molding member is integrally formed in fluid communication with the distal isolation member, where an expanded length of the molding member is adjustable according to the adjusted position of the secondary sheath relative to the molding member and the adjusted distance between the distal and proximal isolation members; and forming the liquid prosthetic material via the molding member into a selected molded shape having an inner diameter substantially larger than the distal portion of the catheter between the first and second isolation members and where the molding member has an expanded profile which is shaped to be different from an expanded profile of the first and second isolation members.

11. The method of claim 10, wherein the length of the expanded molding member is adjustable by axially moving the secondary sheath over a portion of the molding member, the secondary sheath constraining a covered portion of the molding member from expansion.

12. The method of claim 10, further comprising:
allowing the liquid prosthetic material to harden into a prosthesis.

13. The method of claim 10, further comprising:
curing the liquid prosthetic material to form a prosthesis.

14. The method of claim 13, wherein said curing step comprises adding a hardening agent to the liquid prosthetic material.

15. The method of claim 13, wherein said curing step comprises:
applying ultraviolet, radio frequency, laser, infrared, or microwave energy to the liquid prosthetic material.

16. The method of claim 10, further comprising: repeating said method of forming a prosthesis at another location in the target vessel or in another target vessel.

17. The method of claim 10, further comprising the step of:
eluting a therapeutic agent from the prosthesis into the wall of the target vessel or into the bloodstream of the patient.

* * * * *